United States Patent [19]

Ibuki et al.

[11] Patent Number: 4,474,964
[45] Date of Patent: Oct. 2, 1984

[54] 3-AMINOINDAZOLE DERIVATIVES

[75] Inventors: Tadayuki Ibuki; Taisuke Sugihara; Hiromu Kawakubo; Takanori Sone, all of Nobeoka, Japan

[73] Assignee: Asahi, Kasei, Kogyo, Kabushiki, Kaisha, Tokyo, Japan

[21] Appl. No.: 569,524

[22] Filed: Jan. 9, 1984

Related U.S. Application Data

[63] Continuation of Ser. No. 302,989, Sep. 17, 1981.

[30] Foreign Application Priority Data

Sep. 18, 1980 [JP] Japan ................................ 55-128610
Sep. 19, 1980 [JP] Japan ................................ 55-129090

[51] Int. Cl.³ .................. C07D 401/12; C07D 403/12
[52] U.S. Cl. .................................. 546/199; 544/371; 548/359; 548/372; 260/245.6
[58] Field of Search .............. 548/359, 372; 544/371; 546/199; 260/245.6

[56] References Cited

U.S. PATENT DOCUMENTS 3,470,194  9/1969  Palazzo ................. 548/372
3,681,382  8/1972  Gschwend ............. 544/371
3,725,431  4/1973  Gschwend ............. 548/359

Primary Examiner—Robert W. Ramsuer
Attorney, Agent, or Firm—Finnegan, Henderson, Farabow, Garrett & Dunner

[57] ABSTRACT

A compound of the formula (I):

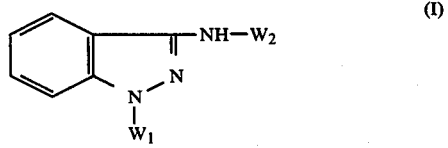

wherein
$W_1$ is a hydrogen atom or a

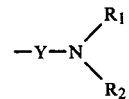

group wherein Y is a $C_{1-6}$ alkylene group or a $C_{1-6}$ alkylene group having a $C_{1-6}$ alkyl group substituent; and $R_1$ and $R_2$ each independently is a hydrogen atom or a $C_{1-6}$ alkyl group and $R_1$ and $R_2$ may form a $C_{4-6}$ heterocyclic ring or a nitrogen-containing $C_{4-6}$ heterocyclic ring together with the adjacent nitrogen atom and the $C_{4-6}$ heterocyclic rings may have at least one $C_{1-6}$ alkyl group, hydroxyl group or halogen atom;
$W_2$ is a hydrogen atom or a

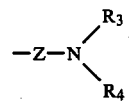

group wherein Z is a $C_{1-6}$ alkylene group or a $C_{1-6}$ alkylene group having a $C_{1-6}$ alkyl group substituent; and $R_3$ and $R_4$ each independently is a hydrogen atom or a $C_{1-6}$ alkyl group and $R_3$ and $R_4$ may form a $C_{4-6}$ heterocyclic ring or a nitrogen-containing $C_{4-6}$ heterocyclic ring together with the adjacent nitrogen atom and the $C_{4-6}$ heterocyclic rings may have at least one $C_{1-6}$ alkyl group, hydroxyl group or halogen atom;
when $W_1$ is a hydrogen atom, $W_2$ is the

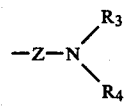

group; and
when $W_2$ is a hydrogen atom, $W_1$ is the

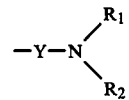

group;
and the pharmaceutically acceptable acid addition salt thereof having antiinflammatory, analgesic and digestive tract ulcer suppressing activity.

7 Claims, No Drawings

3-AMINOINDAZOLE DERIVATIVES

This is a continuation of application Ser. No. 302,989, filed Sept. 17, 1981.

BACKGROUND OF THE INVENTION

1. Field of the Invention

This invention relates to novel 3-aminoindazole derivatives which are useful in therapeutics. More specifically, this invention relates to novel 3-aminoindazole derivatives which have valuable effects for anti-inflammation, analgesic activity and for suppressing digestive tract ulcers, a side effect caused by using acidic non-steroidal anti-inflammatory drugs. Further, this invention relates to a process for preparing the 3-aminoindazole derivatives.

2. Description of the Prior Art

Various experiments to obtain novel and useful anti-inflammatory drugs by many researchers in the field of synthetic organic chemistry have been done. Most of the experiments relate to the synthesis or testing of steroidal hormone compounds such as corticosteroids, and acidic non-steroidal substances such as phenylbutazon and indomethacin. On the other hand, the effects of basic non-steroidal agents have not been reported in development of novel, superior and improved anti-inflammatory agents, even though the basic non-steroidal agents have the same effects as the usual acidic non-steroidal compounds, and further, the basic agents advantageously show almost no side effects such as digestive tract ulcers, caused by the acidic non-steroidal compounds.

3-Aminoindazole was first reported in Bamberger, Liebigs Ann., 305, 339 (1899).

A 3-aminoindazole derivative whose phenyl ring has a halogen group or a trifluoromethyl group and whose 3-position is an amino group or an amino group substituted with a lower alkyl group is described in U.S. Pat. No. 3,133,081. This patent discloses usage of these compounds as drugs having central nervous system activity, and as muscle relaxants, analgesics, antipyretics and tranquilizers. However, pharmacological data of the derivatives are not disclosed. Moreover, the compounds of U.S. Pat. No. 3,133,081 have never been actually used as medicines.

Silvest et. al., Arzneim-Forsch, 16, 59 (1966) report that 1-benzyl-3-(3-dimethylaminopropoxy)indazole hydrochloric acid is effective against primary inflammation. For example, benzydamine hydrochloride is actually used as a medicine.

U.S. Pat. No. 3,681,382 discloses other 3-aminoindazole derivatives wherein the hydrogen atom linked with the 1-position nitrogen atom is substituted by an aryl group and whose 3-position is substituted by a ω-aminoalkyl group or an ω-heterocyclic aminoalkyl group having 1 to 5 carbon atoms together with the nitrogen atom; or a substituted ω-aminoalkylamido group or an ω-heterocyclic aminoalkylamido group having 1 to 5 carbon atoms together with the nitrogen atom. The patent also discloses usage of these compounds as antidepressants and anti-inflammatory drugs. However, pharmacological data are not disclosed in the U.S. patent. Moreover, these compounds have never been actually used as medicines.

Though some indazole derivatives are known, as described above, the prior art fails to teach or suggest the 3-aminoindazole derivatives of this invention.

SUMMARY OF THE INVENTION

According to the present invention in one embodiment there is provided a 3-aminoindazole derivative of the formula (I):

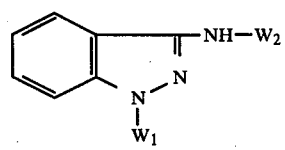

wherein $W_1$ is a hydrogen atom or a

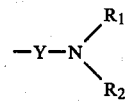

group wherein Y is a $C_{1-6}$ alkylene group or a $C_{1-6}$ alkylene group having a $C_{1-6}$ alkyl group substituent; and $R_1$ and $R_2$ each independently is a hydrogen atom or a $C_{1-6}$ alkyl group and $R_1$ and $R_2$ may form a $C_{4-6}$ heterocyclic ring or a nitrogen-containing $C_{4-6}$ heterocyclic ring together with the adjacent nitrogen atom and the $C_{4-6}$ heterocyclic rings may have at least one $C_{1-6}$ alkyl group, hydroxyl group or halogen atom as a substituent thereof;

$W_2$ is a hydrogen atom or a

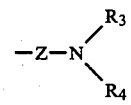

group wherein Z is a $C_{1-6}$ alkylene group or a $C_{1-6}$ alkylene group having a $C_{1-6}$ alkyl group substituent; $R_3$ and $R_4$ each independently is a hydrogen atom or a $C_{1-6}$ alkyl group and $R_3$ and $R_4$ may form a $C_{4-6}$ heterocyclic ring or a nitrogen-containing $C_{4-6}$ heterocyclic ring together with the adjacent nitrogen atom and the $C_{4-6}$ heterocyclic rings may have at least one $C_{1-6}$ alkyl group, hydroxyl group or halogen atom as a substituent thereof;

when $W_1$ is a hydrogen atom, $W_2$ is the

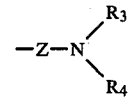

group; and when $W_2$ is a hydrogen atom, $W_1$ is the

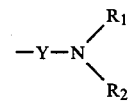

group;

and the pharmaceutically acceptable acid addition salt thereof.

The present invention in another embodiment provides a process for preparing the above described 3-aminoindazole.

DETAILED DESCRIPTION OF THE INVENTION

The 3-aminoindazole derivatives of the formula (I) of this invention are also represented by the following three formulae (II), (III) and (IV):

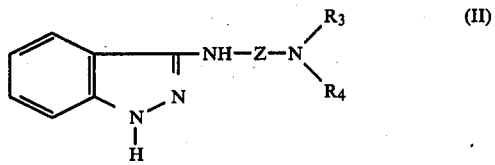

wherein Z, $R_3$ and $R_4$ are the same as defined in the formula (I), and preferably, Z is a $C_{1-6}$ alkylene group or propylene group having a $C_{1-4}$ alkyl group substituent; and $R_3$ and $R_4$ each independently is a $C_{1-6}$ alkyl group and $R_3$ and $R_4$ may form a $C_{4-6}$ heterocyclic ring or a nitrogen-containing $C_{4-6}$ heterocyclic ring together with the adjacent nitrogen atom and the $C_{4-6}$ heterocyclic rings may have at least one methyl group, hydroxyl group, chlorine atom, bromine atom or iodine atom as a substituent thereof:

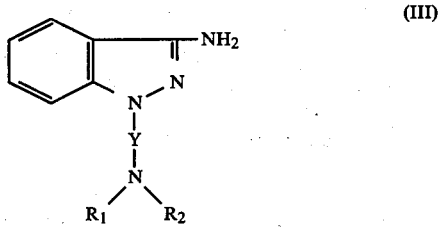

wherein Y, $R_1$ and $R_2$ are the same as defined in the formula (I), and preferably, Y is a $C_{1-6}$ alkylene group or propylene group having a $C_{1-4}$ alkyl group substituent; and $R_1$ and $R_2$ each independently is a $C_{4-6}$ alkyl group and $R_1$ and $R_2$ may form a $C_{4-6}$ heterocyclic ring or a nitrogen-containing $C_{4-6}$ heterocyclic ring together with the adjacent nitrogen atom and the $C_{4-6}$ heterocyclic rings may have at least one methyl group, hydroxyl group, chlorine atom, bromine atom or iodine atom:

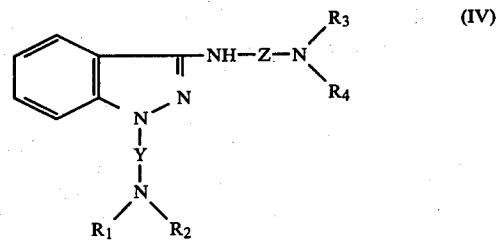

wherein Y, Z, $R_1$, $R_2$, $R_3$ and $R_4$ are the same as defined in the formula (I), and preferably, Y is a $C_{1-4}$ alkylene group or propylene group having a $C_{1-4}$ alkyl group substituent; $R_1$ and $R_2$ each independently is a $C_{1-4}$ alkyl group and $R_1$ and $R_2$ may form a $C_{4-6}$ heterocyclic ring or a nitrogen-containing $C_{4-6}$ heterocyclic ring together with the adjacent nitrogen atom; Z is a $C_{1-6}$ alkylene group or propylene group having a $C_{1-4}$ alkyl group substituent; and $R_3$ and $R_4$ each independently is a $C_{1-4}$ alkyl group and $R_3$ and $R_4$ may form a $C_{4-6}$ heterocyclic ring or a nitrogen-containing $C_{4-6}$ heterocyclic ring together with the adjacent nitrogen atom.

Preferred Z groups in the formula (II) include ethylene group, n-propylene group, n-hexylene group, 3-methylpropylene group and 3-(2-methylpropyl)propylene group.

Preferred

groups in the formula (II) include dimethylamino group, diethylamino group, di-n-propylamino group, di-n-butylamino group, pyrrolidino group, piperidino group, homopiperidino group, piperazino group, 2-methylpiperidino group, 2,6-dimethylpiperidino group, 4-hydroxypiperidino group 4-chloropiperidino group and 4-methylpiperazino group.

Preferred Y groups in the formula (III) includes ethylene group, n-propylene group, n-hexylene group, 3-methylpropylene group and 3-(2-methylpropyl)propylene group.

Preferred

groups in the formula (III) include dimethylamino group, diethylamino group, di-n-propylamino group, di-n-butylamino group, pyrrolidino group, piperidino group, homopiperidino group, piperazino group, 2-methylpiperidino group, 2,6-dimethylpiperidino group, 4-hydroxypiperidino group, 4-chloropiperidino group and 4-methylpiperazino group.

Preferred Y groups in the formula (IV) include ethylene group, n-propylene group, 3-methylpropylene group and 3-(2-methylpropyl)propylene group.

Preferred Z groups in the formula (IV) include ethylene group, n-propylene group, n-hexylene group, 3-methylpropylene group and 3-(2-methylpropyl)propylene group.

Preferred

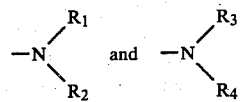

groups in the formula (IV) include dimethylamino group, diethylamino group, di-n-propylamino group, di-n-butylamino group, pyrrolidino group, piperidino group, homopiperidino group and piperazino group.

Exemplary 3-aminoindazole derivatives of this invention include:

(1) 3-(2-piperidinoethylamino)indazole [referred to as "Compound (1)"];
(2) 3-(3-piperidinopropylamino)indazole [referred to as "Compound (2)"];
(3) 3-(6-piperidinohexylamino)indazole [referred to as "Compound (3)"];
(4) 3-(3-pyrrolidinopropylamino)indazole [referred to as "Compound (4)"];
(5) 3-(3-homopiperidinopropylamino)indazole [referred to as "Compound (5)"];

(6) 3-{3-(2-methylpiperidino)propylamino}indazole [referred to as "Compound (6)"];
(7) 3-{3-(2,6-dimethylpiperidino)propylamino}indazole [referred to as "Compound (7)"];
(8) 3-{3-(4-hydroxypiperidino)propylamino}indazole [referred to as "Compound (8)"];
(9) 3-{3-(4-chloropiperidino)propylamino}indazole [referred to as "Compound (9)"];
(10) 3-(3-diethylaminopropylamino)indazole [referred to as "Compound (10)"];
(11) 3-(3-di-n-butylaminopropylamino)indazole [referred to as "Compound (11)"];
(12) 3-(2-dimethylaminoethylamino)indazole [referred to as "Compound (12)"];
(13) 3-{3-(4-methylpiperazino)propylamino}indazole [referred to as "Compound (13)"];
(14) 3-(3-piperidinobutylamino)indazole [referred to as "Compound (14)"];
(15) 3-(5-methyl-3-piperidinohexylamino)indazole [referred to as "Compound (15)"];
(16) 3-(3-diethylaminobutylamino-indazole [referred to as "Compound (16)"];
(17) 1-(2-piperidinoethyl)-3-aminoindazole [referred to as "Compound (17)"];
(18) 1-(3-piperidinopropyl)-3-aminoindazole [referred to as "Compound (18)"];
(19) 1-(6-piperidinohexyl)-3-aminoindazole [referred to as "Compound (19)"];
(20) 1-(3-pyrrolidinopropyl)-3-aminoindazole [referred to as "Compound (20)"];
(21) 1-(3-homopiperidinopropyl)-3-aminoindazole [referred to as "Compound (21)"];
(22) 1-{3-(2-methylpiperidino)propyl}-3-aminoindazole [referred to as "Compound (22)"];
(23) 1-{3-(2,6-dimethylpiperidino)propyl}-3-aminoindazole [referred to as "Compound (23)"];
(24) 1-{3-(4-hydroxypiperidino)propyl}-3-aminoindazole [referred to as "Compound (24)"];
(25) 1-{3-(4-chloropiperidino)propyl}-3-aminoindazole [referred to as "Compound (25)"];
(26) 1-(3-diethylaminopropyl)-3-aminoindazole [referred to as "Compound (26)"];
(27) 1-(3-di-n-butylaminopropyl)-3-aminoindazole [referred to as "Compound (27)"];
(28) 1-(2-dimethylaminoethyl)-3-aminoindazole [referred to as "Compound (28)"];
(29) 1-(3-piperidinobutyl)-3-aminoindazole [referred to as "Compound (29)"];
(30) 1-(5-methyl-3-piperidinohexyl)-3-aminoindazole [referred to as "Compound (30)"];
(31) 1-(3-dimethylamino-5-methylhexyl)-3-aminoindazole [referred to as "Compound (31)"];
(32) 1-{3-(4-methylpiperazino)propyl}-3-aminoindazole [referred to as "Compound (32)"];
(33) 1-(3-diethylaminopropyl)-3-(3-diethylaminopropylamino)indazole [referred to as "Compound (33)"];
(34) 1-(3-diethylaminopropyl)-3-(3-piperidinopropylamino)indazole [referred to as "Compound (34)"];
(35) 1-(3-diethylaminopropyl)-3-(6-piperidinopropylamino)indazole [referred to as "Compound (35)"];
(36) 1-(3-diethylaminopropyl)-3-(3-di-n-butylaminopropylamino)indazole [referred to as "Compound (36)"];
(37) 1-(3-diethylaminopropyl)-3-(3-piperidinobutylamino)indazole [referred to as "Compound (37)"];
(38) 1-(3-piperidinopropyl)-3-(3-diethylaminopropylamino)indazole [referred to as "Compound (38)"];
(39) 1-(3-piperidinopropyl)-3-(3-piperidinopropylamino)indazole [referred to as "Compound (39)"];
(40) 1-(3-piperidinopropyl)-3-(6-piperidinopropylamino)indazole [referred to as "Compound (40)"];
(41) 1-(3-piperidinopropyl)-3-(3-piperidinobutylamino)indazole [referred to as "Compound (41)"];
(42) 1-(3-piperidinobutyl)-3-(3-diethylaminopropylamino)indazole [referred to as "Compound (42)"];
(43) 1-(3-piperidinobutyl)-3-(3-piperidinopropylamino)indazole [referred to as "Compound (43)"];
(44) 1-(3-piperidinobutyl)-3-(5-methyl-3-piperidinohexylamino)indazole [referred to as "Compound (44)"];
(45) 1-(3-piperidinobutyl)-3-(3-dimethylamino-5-methylhexylamino)indazole [referred to as "Compound (45)"];
(46) 1-(3-dimethylaminobutyl)-3-(3-diethylaminopropylamino)indazole [referred to as "Compound (46)"];
(47) 1-(3-dimethylaminobutyl)-3-(3-piperidinopropylamino)indazole [referred to as "Compound (47)"];
(48) 1-(3-dimethylaminobutyl)-3-(3-piperidinobutylamino)indazole [referred to as "Compound (48)"];
(49) 1-(3-dimethylaminobutyl)-3-(3-diethylamino-5-methylhexylamino)indazole [referred to as "Compound (49)"].

The compounds of formula (II) of this invention can be prepared by reacting 3-aminoindazole with an ω-halogenoalkylamine of the general formula (V) in accordance with the following equation:

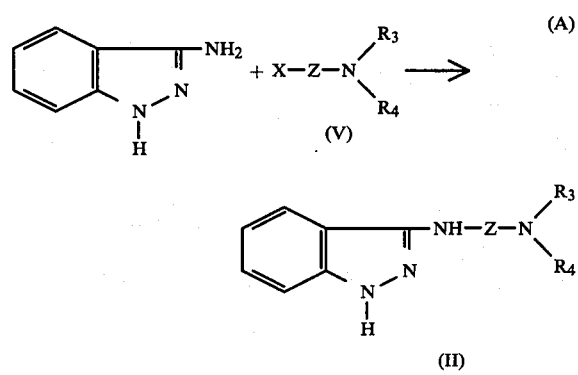

wherein Z, $R_3$ and $R_4$ are the same as defined in the formula (II); and X is a chlorine atom, a bromine atom or an iodine atom.

The 3-aminoindazole is a known compound and can be easily prepared by known synthetic methods such as the one described in C. E. KWARTLER et al., J. Amer. Chem. Soc., 65, 1804 (1943).

The ω-halogenoalkylamine (V) can be prepared by the ordinary synthetic method such as the one described in C. S. Marvel et. al., J. Am. Chem. Soc., 49, 2299 (1927) and H. C. Brill, J. Am. Chem. Soc., 47, 1134 (1925), by using dialkyl halides which correspond to an desired ω-halogenoalkylamines (V).

The ω-halogenoalkylamines (V) which can be employed include 1-(2-chloroethyl)piperidine, 1-(2-bromoethyl)piperidine, 1-(2-iodoethyl)piperidine, 1-(3-chloropropyl)piperidine, 1-(3-bromopropyl)piperidine, 1-(3-iodopropyl)piperidine, 1-(6-chlorohexyl)piperidine, 1-(6-bromohexyl)piperidine, 1-(6-iodohexyl)piperidine, 1-(3-chloropropyl)pyrrolidine, 1-(3-bromopropyl)pyrrolidine, 1-(3-iodopropyl)pyrrolidine, 1-(3-chloropropyl)homopiperidine, 1-(3-bromopropyl)homopiperidine, 1-(3-iodopropyl)homopiperidine, 1-(3-chloropropyl)-2-methylpiperidine, 1-(3-bromopropyl)-2-methylpiperidine, 1-(3-iodopropyl)-2-methylpiperidine, 1-(3-chloropropyl)-2,6-dimethylpiperidine, 1-(3-bromopropyl)-2,6-dimethylpiperidine, 1-(3-iodopropyl)-2,6-dimethylpiperidine, 1-(3-chloropropyl)-4-hydroxypiperidine, 1-(3-bromopropyl)-4-hydroxypiperidine, 1-(3-iodopropyl)-4-hydroxypiperidine, 1-(3-chloropropyl)-4-chloropiperidine, 1-(3-bromopropyl)-4-chloropiperidine, 1-(3-iodopropyl)-4-chloropiperidine, N,N-diethyl-3-chloropropylamine, N,N-diethyl-3-bromopropylamine, N,N-diethyl-3-iodopropylamine, N-(3-chloropropyl)dibutylamine, N-(3-bromopropyl)dibutylamine, N-(3-iodopropyl)dibutylamine, N,N-dimethyl-2-chloroethylamine, N,N-dimethyl-2-bromoethylamine, N,N-dimethyl-2-iodoethylamine, 1-(3-chloropropyl)-4-methylpiperazine, 1-(3-bromopropyl)-4-methylpiperazine, 1-(3-iodopropyl)-4-methylpiperazine, 1-(1-methyl-3-chloropropyl)piperidine, 1-(1-methyl-3-bromopropyl)piperidine, 1-(1-methyl-3-iodopropyl)piperidine, 1-(1-isobutyl-3-chloropropyl)piperidine, 1-(1-isobutyl-3-bromopropyl)piperidine, 1-(1-isobutyl-3-iodopropyl)piperidine, N,N-diethyl-3-chloro-1-methylpropylamine, N,N-diethyl-3-bromo-1-methyl-propylamine, N,N-diethyl-3-iodo-1-methylpropylamine, N,N-diethyl-3-chloro-1-isobutylpropylamine, N,N-diethyl-3-bromo-1-isobutylpropylamino, N,N-diethyl-3-iodo-1-isobutylpropylamine, N,N-dimethyl-3-chloro-1-methylpropylamine, N,N-dimethyl-3-bromo-1-methylpropylamine, N,N-dimethyl-3-iodo-1-methylpropylamine, N,N-dimethyl-3-chloro-1-isobutylpropylamine, N,N-dimethyl-3-bromo-1-isobutylpropylamine and N,N-dimethyl-3-iodo-1-isobutylpropylamine.

The amount of the ω-halogenoalkylamine (V) employed is preferably about 1 mol per mol of the 3-aminoindazole.

The reaction (A) is carried out in the presence of a reaction medium. Exemplary reaction media which can be employed include non-proton polar solvents such as acetonitrile, dimethyl sulfoxide, N,N-dimethylformamide; alcohols such as methyl alcohol, ethyl alcohol and propyl alcohol; and glycols such as ethylene glycol and propylene glycol.

The reaction (A) can be carried out in the presence of an acid acceptor for hydrogen halides which is generated in the reaction. Exemplary acid acceptors which can be employed include tertiary amines such as pyridine and triethylamine; alkali metal carbonates such as potassium carbonate; alkali metal bicarbonates such as sodium hydrogencarbonate; and alkali metal hydroxides such as sodium hydroxide.

The amount of the acid acceptor employed is preferably about 2 mol per mol of the 3-aminoindazole.

The reaction (A) can be carried out at a temperature of from about 10° C. to about 200° C. and preferably from about 80° C. to about 120° C.

The compounds of formula (II) of this invention can also be prepared by reacting a 3-halogenoindazole with an aminoalkylamine compound of the general formula (VI) in the presence of an acid acceptor in accordance with the following equation:

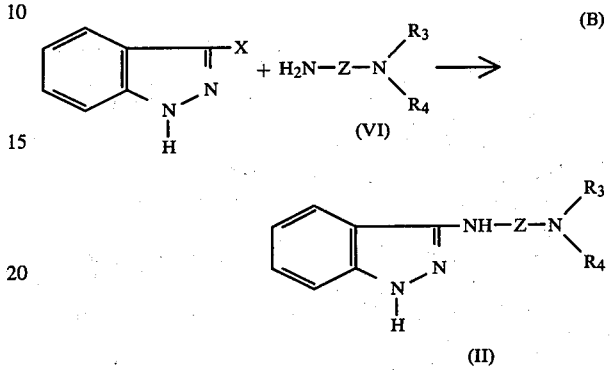

wherein Z, $R_3$ and $R_4$ are the same as defined in the formula (II); and X is a chlorine atom, a bromine atom or an iodine atom.

The 3-halogenoindazole can be prepared by the method described in Org. Syntheses, Coll. Vol. III, 475 (1955).

The aminoalkylamine compound (VI) can be prepared by the ordinary synthetic method described in Org. Syntheses, Coll. Vol. II, 83 (1943), by using halogenoalkyl compounds which correspond to the desired aminoalkylamines (VI).

The aminoalkylamine compounds (VI) which can be employed include 2-piperidinoethylamine, 3-piperidinopropylamine, 6-piperidinohexylamine, 3-pyrrolidinopropylamine, 3-homopiperidinopropylamine, 3-(2-methylpiperidino)propylamine, 3-(2,6-dimethylpiperidino)propylamine, 3-(4-hydroxypiperidino)propylamine, 3-(4-chloropiperidino)propylamine, N,N-diethyl-1,3-propanediamine, N,N-dibutyl-1,3-propanediamine, N,N-dimethyl-1,2-ethanediamine, 3-(4-methylpiperadino)propylamine, 3-methyl-3-piperidinopropylamine, 3-isobutyl-3-piperidinopropylamine, 3-diethylaminobutylamine, 3-diethylamino-5-methylhexylamine, 3-dimethylaminobutylamine and 3-dimethylamino-5-methylhexylamine.

The amount of the aminoalkylamine (VI) which can be employed is preferably about 1 mol per mol of the 3-halogenoindazole.

The reaction (B) is carried out in the presence of a reaction medium. Exemplary reaction media which can be employed include non-proton polar solvents such as acetonitrile, dimethyl sulfoxide and N,N-dimethylformamide; halogenated hydrocarbons such as chloroform, methylene chloride, carbon tetrachloride and 1,2-dichloroethane; alcohols such as methyl alcohol, ethyl alcohol and propyl alcohol; and glycols such as ethylene glycol and propylene glycol.

The reaction (B) can be carried out in the presence of an acid acceptor for hydrogen halides which is generated in the reaction. Exemplary acid acceptors which can be employed include tertiary amines such as pyridine and triethylamine; alkali metal carbonates such as potassium carbonate; alkali metal bicarbonates such as sodium hydrogencarbonate; and alkali metal hydroxides such as sodium hydroxide.

The amount of the acid acceptor employed is preferably about 2 mol per mol of the 3-halogenoindazole.

The reaction (B) can be carried out at a temperature of from about 0° C. to about 200° C. and preferably from about 35° C. to about 120° C.

Another method for preparing the compound of the formula (II) is to react a 2-amino-1-(aminoalkyl)benzamide (VII) with sodium nitrite and hydrochloric acid in water, reduce the reactant with sulfurous acid, and then treat with hydrochloric acid in accordance with the following equations:

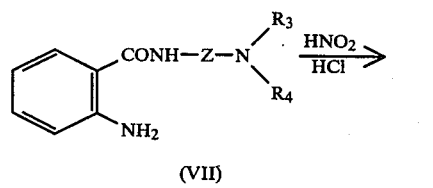

(VII)

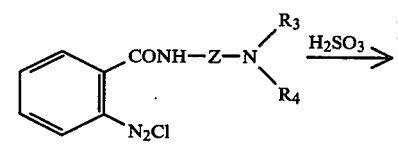

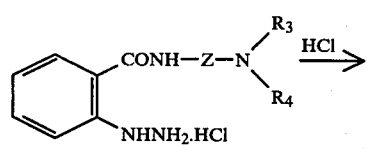

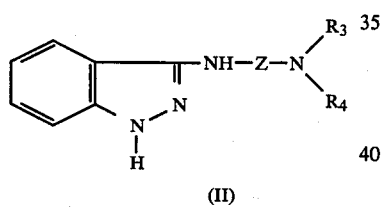

(II)

wherein Z, $R_3$ and $R_4$ are the same as defined in the formula (II).

The 2-amino-1-(aminoalkyl)benzamides (VII) which can be employed include 2-amino-1-(2-piperidinoethyl)benzamide, 2-amino-1-(3-piperidinopropyl)benzamide, 2-amino-1-(6-piperidinohexyl)benzamide, 2-amino-1-(3-pyrrolidinopropyl)benzamide, 2-amino-1-(3-homopiperidinopropyl)benzamide, 2-amino-1-[3-(2-methylpiperidino)propyl]benzamide, 2-amino-1-[3-(2,6-dimethylpiperidino)propyl]benzamide, 2-amino-1-[3-(4-hydroxypiperidino)propyl]benzamide, 2-amino-1-[3-(4-chloropiperidino)propyl]benzamide, 2-amino-1-(3-diethylaminopropyl)benzamide, 2-amino-1-(3-dibutylaminopropyl)benzamide, 2-amino-1-(2-dimethylaminoethyl)benzamide, 2-amino-1-[3-(4-methylpiperazino)propyl]benzamide, 2-amino-1-(3-piperidinobutyl)benzamide, 2-amino-1-(5-methyl-3-piperidinohexyl)benzamide, 2-amino-1-(3-diethylaminobutyl)benzamide, 3-amino-1-(3-diethylamino-5-methylhexyl)benzamide, 2-amino-1-(3-dimethylaminobutyl)benzamide and 2-amino-1-(3-dimethylamino-5-methylhexyl)benzamide.

The reaction (C) can be carried out at a temperature of from about −20° C. to about 20° C. and preferably from about 0° C. to 10° C.

The compounds of formula (III) can be prepared by reacting 3-aminoindazole with phthalic anhydride to obtain 3-phthalimidoindazole, reacting the 3-phthalimidoindazole with an ω-halogenoalkylamine of the formula (VIII) to give a 1-(aminoalkyl)-3-phthalimidoindazole, and then treating the 1-(aminoalkyl)-3-phthalimidoindazole with hydrazine hydrate to release the protective group of the 3-position amino group in accordance with the following equations:

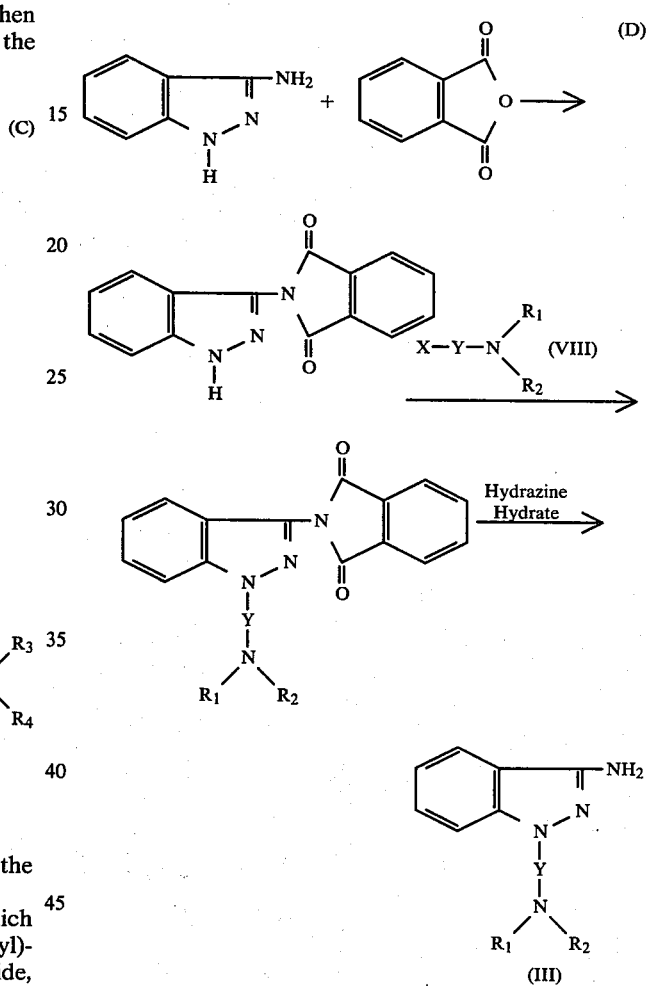

wherein Y, $R_1$ and $R_2$ are the same as defined in the formula (III); and X is a chlorine atom, a bromine atom or an iodine atom.

The reaction between the 3-aminoindazole and phthalic anhydride can be carried out in the presence of a reaction medium. Exemplary reaction media which can be employed include polar organic solvents such as dioxane, diethyl ether, tetrahydrofuran, ethyl alcohol, ethylene glycol, acetonitrile, dimethyl sulfoxide and N,N-dimethylformamide.

The reaction between the 3-aminoindazole and phthalic anhydride can be carried out at a temperature of from about 10° C. to about 200° C. and preferably from about 60° C. to about 150° C.

The reaction between the 3-phthalimidoindazole and the ω-halogenoalkylamine (VIII) can be carried out in the presence of a reaction medium and an acid acceptor. Exemplary reaction media which can be employed include non-proton polar solvents such as acetonitrile, dimethyl sulfoxide and N,N-dimethylformamide; alcohols such as methyl alcohol, ethyl alcohol and propyl alcohol; and glycols such as ethylene glycol and propylene glycol. Exemplary acid acceptors which can be employed include tertiary amines such as pyridine and triethylamine; alkali metal carbonates such as potassium carbonate; alkali metal bicarbonates such as sodium hydrogencarbonate; and alkali metal hydroxides such as sodium hydroxide. The amount of the acid acceptor employed is preferably about 2 mol per mol of the 3-phthalimidoindazole.

The ω-halogenoalkylamines (VIII) which can be employed include 1-(2-chloroethyl)piperidine, 1-(2-bromoethyl)piperidine, 1-(2-iodoethyl)piperidine, 1-(3-chloropropyl)piperidine, 1-(3-bromopropyl)piperidine, 1-(3-iodopropyl)piperidine, 1-(6-chlorohexyl)piperidine, 1-(6-bromohexyl)piperidine, 1-(6-iodohexyl)piperidine, 1-(3-chloropropyl)pyrrolidine, 1-(3-bromopropyl)pyrrolidine, 1-(3-iodopropyl)pyrrolidine, 1-(3-chloropropyl)homopiperidine, 1-(3-bromopropyl)homopiperidine, 1-(3-iodopropyl)homopiperidine, 1-(3-chloropropyl)-2-methylpiperidine, 1-(3-bromopropyl)-2-methylpiperidine, 1-(3-iodopropyl)-2-methylpiperidine, 1-(3-chloropropyl)-2,6-dimethylpiperidine, 1-(3-bromopropyl)-2,6-dimethylpiperidine, 1-(3-iodopropyl)-2,6-dimethylpiperidine, 1-(3-chloropropyl)-4-hydroxypiperidine, 1-(3-bromopropyl)-4-hydroxypiperidine, 1-(3-iodopropyl)-4-hydroxypiperidine, 1-(3-chloropropyl)-4-chloropiperidine, 1-(3-bromopropyl)-4-chloropiperidine, 1-(3-iodopropyl)-4-chloropiperidine, N,N-diethyl-3-chloropropylamine, N,N-diethyl-3-bromopropylamine, N,N-diethyl-3-iodopropylamine, N-(3-chloropropyl)dibutylamine, N-(3-bromopropyl)dibutylamine, N-(3-iodopropyl)dibutylamine, N,N-dimethyl-2-chloroethylamine, N,N-dimethyl-2-bromoethylamine, N,N-dimethyl-2-iodoethylamine, 1-(3-chloropropyl)-4-methylpiperazine, 1-(3-bromopropyl)-4-methylpiperazine, 1-(3-iodopropyl)-4-methylpiperazine, 1-(1-methyl-3-chloropropyl)piperidine, 1-(1-methyl-3-bromopropyl)piperidine, 1-(1-methyl-3-iodopropyl)piperidine, 1-(1-isobutyl-3-chloropropyl)piperidine, 1-(1-isobutyl-3-bromopropyl)piperidine, 1-(1-isobutyl-3-iodopropyl)piperidine, N,N-diethyl-3-chloro-1-methylpropylamine, N,N-diethyl-3-bromo-1-methylpropylamine, N,N-diethyl-3-iodo-1-methylpropylamine, N,N-diethyl-3-chloro-1-isobutylpropylamine, N,N-diethyl-3-bromo-1-isobutylpropylamine, N,N-diethyl-3-iodo-1-isobutylpropylamine, N,N-dimethyl-3-chloro-1-methylpropylamine, N,N-dimethyl-3-bromo-1-methylpropylamine, N,N-dimethyl-3-iodo-1-methylpropylamine, N,N-dimethyl-3-chloro-1-isobutylpropylamine, N,N-dimethyl-3-bromo-1-isobutylpropylamine and N,N-dimethyl-3-iodo-1-isobutylpropylamine.

The reaction between the 3-phthalimidoindazole and the ω-halogenoalkylamine can be carried out at a temperature of from about 10° C. to about 200° C. and preferably from about 80° C. to about 120° C.

The reaction between the 1-(aminoalkyl)-3-phthalimidoindazole and hydrazine hydrate can be carried out in the presence of a reaction medium. Exemplary reaction media which can be employed include alcohols such as methyl alcohol and ethyl alcohol; glycols such as ethylene glycol and propylene glycol; diglyme and triethanolamine. Preferably this reaction can be carried out under cooling with ice.

Another method for preparing the compound of the formula (III) comprises reacting a 2-cyano-1-(aminoalkylamino)benzene (IX) with sodium nitrite and hydrochloric acid in water to obtain a nitroso compound, reducing the nitroso compound with stannous chloride and hydrochloric acid, and then treating the reactant with hydrochloric acid in accordance with the following equations:

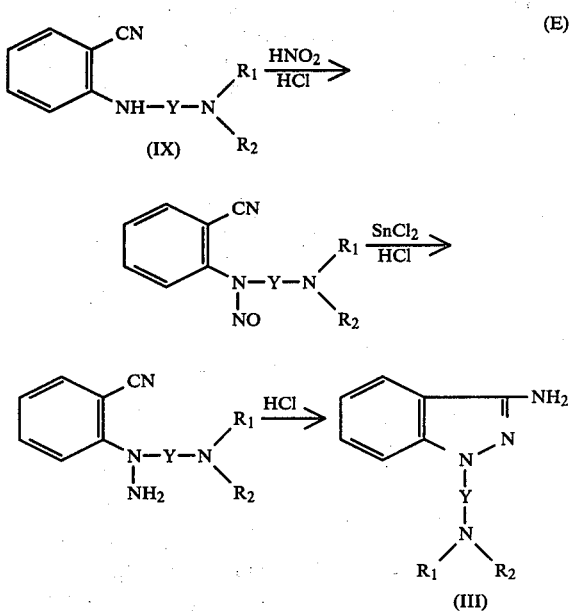

wherein Y, $R_1$ and $R_2$ are the same as defined in the formula (III).

The 2-cyano-1-(aminoalkylamino)benzene (IX) which can be employed include 2-cyano-1-(2-piperidinoethylamino)benzene, 2-cyano-1-(3-piperidinopropylamino)benzene, 2-cyano-1-(6-piperidinohexylamino)benzene, 2-cyano-1-(3-pyrrolidinopropylamino)benzene, 2-cyano-1-(3-homopiperidinopropylamino)benzene, 2-cyano-1-[3-(2-methylpiperidino)propylamino]benzene, 2-cyano-1-[3-(2,6-dimethylpiperidino)propylamino]benzene, 2-cyano-1-[3-(4-hydroxypiperidino)propylamino]benzene, 2-cyano-1-[3-(4-chloropiperidino)propylamino]benzene, 2-cyano-1-(3-diethylaminopropylamino)benzene, 2-cyano-1-(3-dibutylaminopropylamino)benzene, 2-cyano-1-(2-dimethylaminoethylamino)benzene, 2-cyano-1-[3-(4-methylpiperazino)propylamino]benzene, 2-cyano-1-[3-piperidinobutylamino]benzene, 2-cyano-1-(5-methyl-3-piperidinohexylamino)benzene, 2-cyano-1-(3-diethylaminobutylamino)benzene, 2-cyano-1-(3-diethylamino-5-methylhexylamino)benzene, 2-cyano-1-(3-dimethylaminobutylamino)benzene and 2-cyano-1-(3-dimethylamino-5-methylhexylamino)benzene.

The reaction (E) can be carried out at a temperature of from about −20° C. to about 20° C. and preferably from about 0° C. to 10° C.

The compound of the formula (IV) can be prepared by reacting an 1-aminoalkyl-3-aminoindazole of the formula (III) with an ω-halogenoalkylamine compound of the formula (V) in the presence of an acid acceptor in accordance with the following equation:

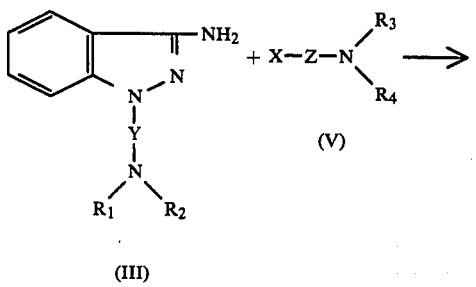

(III)

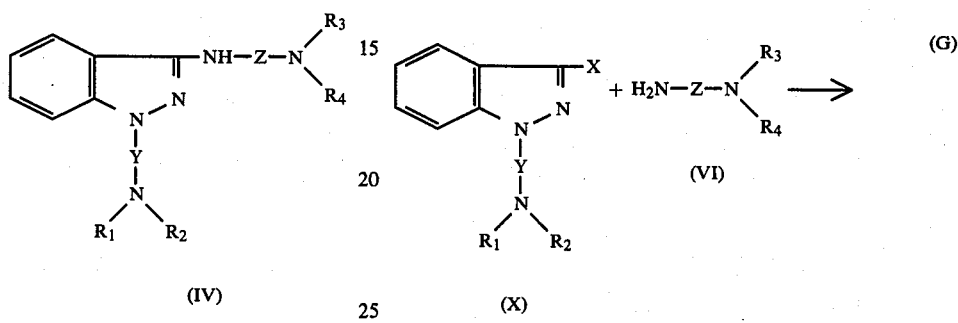

wherein Y, Z, R₁, R₂, R₃ and R₄ are the same as defined in the formula (IV); and X is a chlorine atom, a bromine atom or an iodine atom.

The 1-aminoalkyl-3-aminoindazoles (III) which can be employed in the reaction (F) include 1-(2-piperidinoethyl)-3-aminoindazole, 1-(3-piperidinopropyl)-3-aminoindazole, 1-(6-piperidinohexyl)-3-aminoindazole, 1-(3-pyrrolidinopropyl)-3-aminoindazole, 1-(3-homopiperidinopropyl)-3-aminoindazole, 1-[3-(2-methylpiperidino)propyl]-3-aminoindazole, 1-[3-(2,6-dimethylpiperidino)propyl]-3-aminoindazole, 1-[3-(4-hydroxypiperidino)propyl]-3-aminoindazole, 1-[3-(4-chloropiperidino)propyl]-3-aminoindazole, 1-(3-diethylaminopropyl)-3-aminoindazole, 1-(3-dibutylaminopropyl)-3-aminoindazole, 1-(2-dimethylaminoethyl)-3-aminoindazole, 1-[3-(4-methylpiperazino)propyl]-3-aminoindazole, 1-(3-piperidinobutyl)-3-aminoindazole, 1-(5-methyl-3-piperidinohexyl)-3-aminoindazole, 1-(3-diethylaminobutyl)-3-aminoindazole, 1-(3-diethylamino-5-methylhexyl)-3-aminoindazole, 1-(3-dimethylaminobutyl)-3-aminoindazole and 1-(3-dimethylamino-5-methylhexyl)-3-aminoindazole.

The halogenoalkylamine compounds (V) which can be employed in the reaction (F) include the same ω-halogenoalkylamines used in the reaction (A) of this invention.

The amount of the halogenoalkylamine (V) which can be employed is preferably about 1 mol per mol of the 1-aminoalkyl-3-aminoindazole (III).

The reaction (F) can be carried out in the presence of a reaction medium. Exemplary reaction media which can be employed include non-proton polar solvents such as acetonitrile, dimethyl sulfoxide and N,N-dimethylformamide; alcohols such as methyl alcohol, ethyl alcohol and propyl alcohol; and glycols such as ethylene glycol and propylene glycol.

Exemplary acid acceptors which can be employed in the reaction (F) include tertiary amines such as pyridine and triethylamine; alkali metal carbonates such as potassium carbonate; alkali metal bicarbonates such as sodium hydrogencarbonate; and alkali metal hydroxides such as sodium hydroxide.

The amount of the acid acceptor employed is preferably about 2 mol per mol of the 1-aminoalkyl-3-aminoindazole (III).

The reaction (F) can be carried out at the temperature of from about 10° C. to about 200° C. and preferably from about 80° C. to about 120° C.

The compound of the formula (IV) of this invention can be also prepared by reacting a 1-aminoalkyl-3-halogenoindazole of the formula (X) with an aminoalkylamine compound of the formula (VI) in the presence of an acid acceptor in accordance with the following equation:

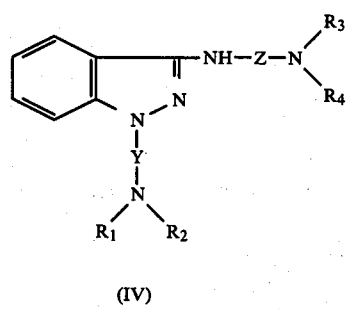

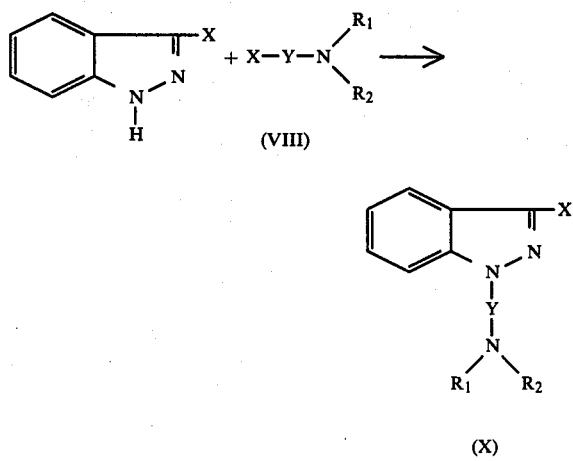

wherein Y, Z, R₁, R₂, R₃ and R₄ are the same as defined in the formula (IV); and X is a chlorine atom, a bromine atom or an iodine atom.

The 1-aminoalkyl-3-halogenoindazole (X) can be prepared by reacting a 3-halogenoindazole with an ω-halogenoalkylamine of the formula (VIII) in the presence of an acid acceptor in accordance with the following equation:

wherein X, Y, R₁ and R₂ are the same as defined in the formula (X).

The ω-halogenoalkylamines (VIII) which can be employed in this reaction include the same ω-halogenoalkylamines used in the reaction (D) of this invention.

The reaction conditions employed are the same as the conditions employed in the reaction (B) of this invention.

The 1-aminoalkyl-3-halogenoindazoles (X) which can be employed in the reaction (G) include 1-(2-piperidinoethyl)-3-chloroindazole, 1-(2-piperidinoethyl)-3-bromoindazole, 1-(2-piperidinoethyl)-3-iodoindazole, 1-(3-piperidinopropyl)-3-chloroindazole, 1-(3-piperidinopropyl)-3-bromoindazole, 1-(3-piperidinopropyl)-3-iodoindazole, 1-(6-piperidinohexyl)-3-chloroindazole, 1-(6-piperidinohexyl)-3-bromoindazole, 1-(6-piperidinohexyl)-3-iodoindazole, 1-(3-pyrrolidinopropyl)-3-chloroindazole, 1-(3-pyrrolidinopropyl)-3-bromoindazole, 1-(3-pyrrolidinopropyl)-3-iodoindazole, 1-(3-homopiperidinopropyl)-3-chloroindazole, 1-(3-homopiperidinopropyl)-3-bromoindazole, 1-(3-homopiperidinopropyl)-3-iodoindazole, 1-[3-(2-methylpiperidino)propyl]-3-chloroindazole, 1-[3-(2-methylpiperidino)propyl]-3-bromoindazole, 1-[3-(2-methylpiperidino)propyl]-3-iodoindazole, 1-[3-(2,6-dimethylpiperidino)propyl]-3-chloroindazole, 1-[3-(2,6-dimethylpiperidino)propyl]-3-bromoindazole, 1-[3-(2,6-dimethylpiperidino)propyl]-3-iodoindazole, 1-[3-(4-hydroxypiperidino)propyl]-3-chloroindazole, 1-[3-(4-hydroxypiperidino)propyl]-3-bromoindazole, 1-[3-(4-hydroxypiperidino)propyl]-3-iodoindazole, 1-[3-(4-chloropiperidino)propyl]-3-chloroindazole, 1-[3-(4-chloropiperidino)propyl]-3-bromoindazole, 1-[3-(4-chloropiperidino)propyl]-3-iodoindazole, 1-(3-diethylaminopropyl)-3-chloroindazole, 1-(3-diethylaminopropyl)-3-bromoindazole, 1-(3-diethylaminopropyl)-3-iodoindazole, 1-(3-dibutylaminopropyl)-3-chloroindazole, 1-(3-dibutylaminopropyl)-3-bromoindazole, 1-(3-dibutylaminopropyl)-3-iodoindazole, 1-(2-dimethylaminoethyl)-3-chloroindazole, 1-(2-dimethylaminoethyl)-3-bromoindazole, 1-(2-dimethylaminoethyl)-3-iodoindazole, 1-[3-(4-methylpiperazino)propyl]-3-chloroindazole, 1-[3-(4-methylpiperazino)propyl]-3-bromoindazole, 1-[3-(4-methylpiperazino)propyl]-3-iodoindazole, 1-(3-piperidinobutyl)-3-chloroindazole, 1-(3-piperidinobutyl)-3-bromoindazole, 1-(3-piperidinobutyl)-3-iodoindazole, 1-(5-methyl-3-piperidinohexyl)-3-chloroindazole, 1-(5-methyl-3-piperidinohexyl)-3-bromoindazole, 1-(5-methyl-3-piperidinohexyl)-3-iodoindazole, 1-(3-diethylaminobutyl)-3-chloroindazole, 1-(3-diethylaminobutyl)-3-bromoindazole, 1-(3-diethylaminobutyl)-3-iodoindazole, 1-(3-diethylamino-5-methylhexyl)-3-chloroindazole, 1-(3-diethylamino-5-methylhexyl)-3-bromoindazole, 1-(3-diethylamino-5-methylhexyl)-3-iodoindazole, 1-(3-dimethylaminobutyl)-3-chloroindazole, 1-(3-dimethylaminobutyl)-3-bromoindazole, 1-(3-dimethylaminobutyl)-3-iodoindazole, 1-(3-dimethylamino-5-methylhexyl)-3-chloroindazole, 1-(3-dimethylamino-5-methylhexyl)-3-bromoindazole and 1-(3-dimethylamino-5-methylhexyl)-3-iodoindazole.

The aminoalkylamine compounds (VI) which can be employed in the reaction (G) include the same aminoalkylamine compounds used in the reaction (B) of this invention.

The amount of the aminoalkylamine (VI) which can be employed is preferably about 1 mol per mol of the 1-aminoalkyl-3-halogenoindazole (X).

The reaction (G) can be carried out in the presence of a reaction medium. Exemplary reaction media which can be employed include non-proton polar solvents such as acetonitrile, dimethyl sulfoxide and N,N-dimethylformamide; halogenated hydrocarbons such as chloroform, methylene chloride, carbon tetrachloride and 1,2-dichloroethane; alcohols such as methyl alcohol, ethyl alcohol and propyl alcohol; and glycols such as ethylene glycol and propylene glycol.

Exemplary acid acceptors which can be employed in the reaction (G) include tertiary amines such as pyridine and triethylamine; alkali metal carbonates such as potassium carbonate; alkali metal bicarbonates such as sodium hydrogencarbonate; and alkali metal hydroxides such as sodium hydroxide. The amount of the acid acceptor employed is preferably about 2 mol per mol of the 1-aminoalkyl-3-halogenoindazole (X).

The reaction (G) can be carried out at a temperature of from about 0° C. to about 200° C. and preferably from about 35° C. to about 120° C.

A third method for preparing the compound of the formula (IV) of this invention comprises reacting a 3-(aminoalkylamino)indazole of the formula (II) with a halogenoalkylamine compound of the formula (VIII) in the presence of an acid acceptor for hydrogen halides generated in the reaction in accordance with the following equation:

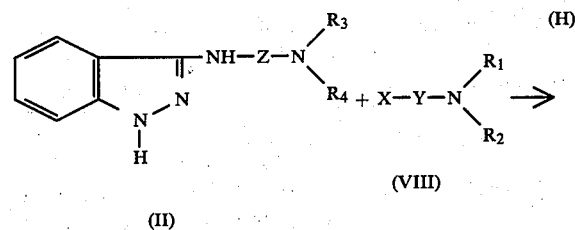

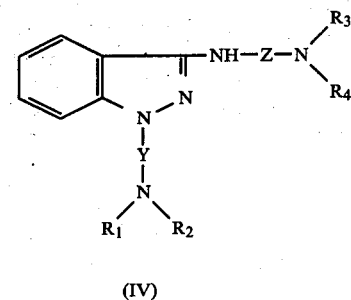

wherein Y, Z, $R_1$, $R_2$, $R_3$ and $R_4$ are the same as defined in the formula (IV); and X is a chlorine atom, a bromine atom or an iodine atom.

The 3-(aminoalkylamino)indazoles of the formula (II) which can be employed in the reaction (H) include 3-(2-piperidinoethylamino)indazole, 3-(3-piperidinopropylamino)indazole, 3-(6-piperidinohexylamino)indazole, 3-(3-pyrrolidinopropylamino)indazole, 3-(3-homopiperidinopropylamino)indazole, 3-[3-(2-methylpiperidino)propylamino]indazole, 3-[3-(2,6-dimethylpiperidino)propylamino]indazole, 3-[3-(4-hydroxypiperidino)propylamino]indazole, 3-[3-(4-chloropiperidino)propylamino]indazole, 3-(3-diethylaminopropylamino)indazole, 3-(3-dibutylaminopropylamino)indazole, 3-(2-dimethylaminoethylamino)indazole, 3-[3-(4-methylpiperazino)propylamino]indazole, 3-(3-piperidinobutylamino)indazole, 3-(5-methyl-3-piperidinohexylamino)indazole, 3-(3-diethylaminobutylamino)indazole, 3-(3-diethylamino-5-methylhexylamino)indazole, 3-(3-dimethylaminobutylamino)indazole and 3-(3-dimethylamino-5-methylhexylamino)indazole.

The halogenoalkylamine compound (VIII) which can be employed in the reaction (H) include the same ω-halogenoalkylamines used in the reaction (D) of this invention.

The amount of the halogenoalkylamine (VIII) which can be employed is preferably about 1 mol per mol of the 3-(aminoalkylamino)indazole (II).

The reaction (H) can be carried out in the presence of a reaction medium. Exemplary reaction media wich can be employed include non-proton polar solvents such as acetonitrile, dimethyl sulfoxide and N,N-dimethylformamide; alcohols such as methyl alcohol, ethyl alcohol and propyl alcohol; and glycols such as ethylene glycol and propylene glycol.

Exemplary acid acceptors which can be employed in the reaction (H) include tertiary amines such as pyridine and triethylamine; alkali metal carbonates such as potassium carbonate; alkali metal bicarbonates such as sodium hydrogencarbonate; and alkali metal hydroxide such as sodium hydroxide.

The amount of the acid acceptor employed is preferably about 2 mol per mol of the 3-(aminoalkylamino)indazole (II).

The reaction (H) can be carried out at a temperature of from about 0° C. to about 200° C. and preferably from about 80° C. to about 120° C.

Another method for preparing the compound of the formula (IV) of this invention comprises reacting a 2-amino-1-(aminoalkyl)benzamide of the formula (VII) with a halogenoalkylamine compound of the formula (VIII) in the presence of an acid acceptor in accordance with the following equations:

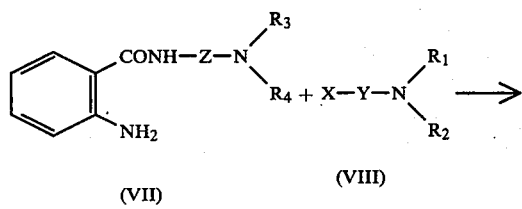

(VII)  (VIII)

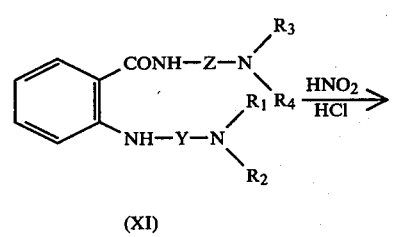

(XI)

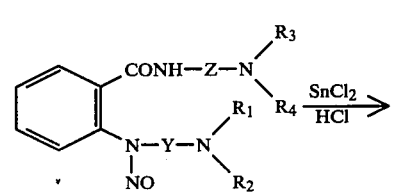

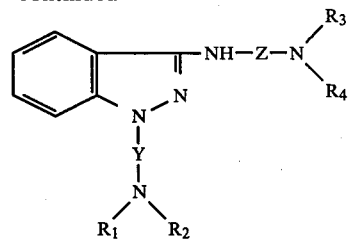

(IV)

wherein Y, Z, $R_1$, $R_2$, $R_3$ and $R_4$ are the same as defined in the formula (VI); and X is a chlorine atom, a bromine atom or an iodine atom.

The 2-amino-1-(aminoalkyl)benzamides (VII) which can be employed in the reaction (I) include the same 2-amino-1-(aminoalkyl)benzamides used in the reaction (C) of this invention.

The halogenoalkylamine compounds (VIII) which can be employed in the reaction (I) include the same ω-halogenoalkylamines used in the reaction (D) of this invention.

The amount of the halogenoalkylamine (VIII) which can be employed is preferably about 1 mol per mol of the 2-amino-1-(aminoalkyl)benzamide (VII).

The reaction between the compound of the formula (VII) and the compound of the formula (VIII) can be carried out in the presence of an acid acceptor and a reaction medium. Exemplary reaction media which can be employed include non-proton polar solvents such as acetonitrile, dimethyl sulfoxide and N,N-dimethylformamide; alcohols such as methyl alcohol, ethyl alcohol and propyl alcohol; and glycols such as ethylene glycol and propylene glycol. Exemplary acid acceptors which can be employed include tertiary amines such as pyridine and triethylamine; alkali metal carbonates such as potassium carbonate; alkali metal bicarbonates such as sodium hydrogencarbonate; and alkali metal hydroxide such as sodium hydroxide.

The amount of the acid acceptor employed is preferably about 2 mol per mol of the 2-amino-1-(aminoalkyl)benzamide (VII).

The reaction between the compound of the formula (VII) and the compound of the formula (VIII) can be carried out at a temperature of from about 0° C. to about 200° C. and preferably from about 80° C. to 120° C.

The compound (XI) is reacted with sodium nitrite and hydrochloric acid to obtain a nitroso compound, and the thus obtained compound is reduced with hydrochloric acid to obtain the compound of the formula (IV). These reactions can be carried out at a temperature of from about −20° C. to about 20° C. and preferably from about 0° C. to about 10° C.

The pharmaceutically acceptable non-toxic acid addition salts of the 3-aminoindazole derivatives of the general formula (I) according to this invention can be prepared by reacting the 3-aminoindazole derivatives with inorganic or organic acids. The amount of the acids which can be employed in this reaction is substantially equimolar of the 3-aminoindazole derivatives. The reaction can be carried out in an aqueous solvent or an organic solvent such as methyl alcohol and ethyl alcohol. After the reaction is completed, the solvent is evaporated carefully to give the salts in a solid state.

Suitable examples of such pharmaceutically acceptable acid addition salts include the salts of inorganic acids such as hydrochloric acid, hydrobromic acid, hydroiodic acid, sulfuric acid, phosphoric acid and nitric acid; the salts of organic acids such as formic acid, acetic acid, propionic acid, succinic acid, lactic acid, maleic acid, fumaric acid, malonic acid, oxalic acid, citric acid, tartric acid, malic acid, mucic acid, gluconic acid, benzoic acid, salicylic acid, 1,5-naphthalenedisulfonic acid, ascorbic acid, phenylacetic acid, p-aminosalicylic acid, methanesulfonic acid, ethanesulfonic acid, hydroxyethanesulfonic acid and p-toluenesulfonic acid; and saccharates.

It has now been found that all the 3-aminoindazole derivatives of the general formula (I) and their pharmaceutically acceptable salts have therapeutic use as anti-inflammatory drugs and analgesic drugs. More specifically, the 3-aminoindazole derivatives and the pharmaceutically acceptable salts of this invention have unique effects as compared with known 3-aminoindazole derivatives, for example, in reducing swelling caused by an inflammatory, abating pain and suppressing digestive tract ulcers, a side effect caused by using acidic nonsteroidal anti-inflammatory drugs.

The therapeutic activities of the 3-aminoindazole derivatives of this invention were measured by the following methods.

ANTI-INFLAMMATORY ACTIVITY

A standard method of Carrageenin Edema Test in Rat's Paw described in C. A. Winter et al., Proc. Soc. Exp. Biol. Med., 111, 544 (1962) was employed.

Female Wistar rats weighing 120–150 g were orally administered 50–100 mg/kg of the test compound as an aqueous solution. One hour later, the pad of a hind paw of the rat was injected with 0.1 ml of 1% aqueous carrageenin solution. The volume of the paw was measured both before the injection of carrageenin and three hours after the injection. The increase in volume of the affected paw of the test animals (one group consisting of 6 animals) to the increase in volume of the affected paw of the controls shows the effect of the test compound. When this effect is the same or superior to the effect obtained by oral administration with 100 mg/kg of the standard compound such as phenylbutazon, the test compound is considered to have anti-inflammatory activity.

The edema inhibition percentage of the test compound was calculated from the ratio of the increase in the volume of the affected paw of the test animals to the increase in the volume of the affected paw of the controls.

ANALGESIC ACTIVITY (1) Acetic Acid-Writhing Test

Acetic acid-writhing test was carried out according to Koster et al., Fed. Proc., 18, 412 (1959). Male ddy-strain mice weighing 15–18 g were orally administered 100 mg/kg of the test compound as an aqueous solution. Thirty minutes later, the mice were intraperitoneally injected with 0.1 ml/10 g of 0.7% acetic acid physiological salt solution as a stimulant. Ten minutes after the stimulant injection, writhing frequency as pain response was observed and recorded over 10 minutes. The difference between the frequency of the injected test animals (one group consisting of 6 animals) and that of the controls shows the effect of the test compound. When the effect is the same or superior to the effect obtained by oral administration with the standard compound such as aspirin, the test compound is considered to have analgesic activity.

The inhibition percentage of the test compound was represented as the ratio of the inhibition of the writhing frequency.

(2) Randall-Selitto Test

The analgesic activity test was carried out according to the general method described in J. O. Randall & J. J. Selitto, Arch. Int. Pharmacodyn, 111, 409 (1957). Female wister rats weighing 120–150 g were orally administered 50 mg/kg of the test compound as an aqueous solution. Thirty minutes later, the pad of a hind paw of the rat was injected with 0.1 ml of 1% aqueous carrageenin solution. Pressure was applied to the paw where edema was formed by Balance-type Pressure Device (Ugo Basile Company; Italy) 1, 2, 3 and 4 hours after the injection. The weight when the test animals began to struggle with pain was measured. The analgesic activity is represented by an analgesic coefficient which is obtained by dividing the average weight measured 1.5, 2.5, 3.5 and 4.5 hours after the administration by the applied weight prior to the administration. When the difference between the reaction of the test animals (one group consisting of 6 animals) and that of the controls is the same or superior to a effect obtained by administration of the basic anti-inflammatory analgesic such as tiaramide, the test compound is recognized as an effective compound for treating pain.

Acute Toxicity

Acute toxicity was measured by an ordinary method described in Finney D. J. Probit Analysis Cambridge University Press 48, (1952). Ddy mice weighing about 18 g on average, each group consisting of 10 animals, were intraperitoneally injected with the physiological salt solution containing the test compound. The amount of the test compound administered was varied in 5–8 groups. Three days after the administration, dead animals were counted in each group. The amount of the test compound killing half the number of the animals ($LD_{50}$) was calculated from the results.

Anti-Ulcer Test

The test compound was suspended in 1% HCO-60 (trade name for polyoxyethylene hydrogenated castor oil; a product of Nikko Chemical Co., Ltd., Japan) at the concentration of 10 mg/ml. Male donryu rats weighing 150–160 g were orally administered 100 mg/kg of the test compound. The occurrence of gastric ulcer was examined 24 hours after the administration.

The following test results show the effects of the compounds according to this invention.

The anti-inflammatory activity of the 3-aminoindazole derivative hydrochloric acid salts of this invention was measured. The activity is evaluated with respect to whether the effect of inhibition shows a statistically significant difference (20%). The results of Carrageenin edema tests are shown in Table 1.

TABLE 1

| 3-Aminoindazole Derivative | Compound No. | Dose (mg/kg) | Inhibition (%) |
|---|---|---|---|
| 3-(3-Piperidinopropylamino)indazole | (2) | 100 | 55 |
| 3-(3-Pyrrolidinopropylamino)indazole | (4) | 100 | 30 |

TABLE 1-continued

| 3-Aminoindazole Derivative | Compound No. | Dose (mg/kg) | Inhibition (%) |
|---|---|---|---|
| 3-[3-(2-Methylpiperidino)propylamino]indazole | (6) | 100 | 67 |
| 3-(3-Diethylaminopropylamino)indazole | (10) | 100 | 66 |
| 3-[3-(4-Methylpiperazino)propylamino]indazole | (13) | 100 | 30 |
| 1-(3-Piperidinopropyl)-3-aminoindazole | (18) | 100 | 54 |
| 1-[3-(2-Methylpiperidino)propyl]-3-aminoindazole | (22) | 100 | 51 |
| 1-(2-Dimethylaminoethyl)-3-aminoindazole | (28) | 100 | 44 |
| 1-(3-Diethylaminopropyl)-3-(3-diethylaminopropyl-amino)indazole | (33) | 100 | 29 |
| 1-(3-Diethylaminopropyl)-3-(piperidinopropyl-amino)indazole | (34) | 100 | 28 |
| 1-(3-Piperidinopropyl)-3-(3-diethylaminopropyl-amino)indazole | (38) | 100 | 29 |
| 1-(3-Piperidinopropyl)-3-(3-piperidinopropyl-amino)indazole | (39) | 100 | 28 |
| 3-(Propylamino)indazole (comparative Compound) | C-1 | 100 | 7 |
| 1-Propyl-3-aminoindazole (comparative Compound) | C-2 | 100 | 7 |
| 1-(2-Phenylethyl)-3-aminoindazole (comparative Compound) | C-3 | 100 | 7 |

In Table 1, 3-(propylamino)indazole [referred to as "Compound C-1"]; 1-propyl-3-aminoindazole [referred to as "Compound C-2"] and 1-(2-phenylethyl)-3-aminoindazole [referred to as "Compound C-3"] are all comparative compounds.

Inhibition values of the compounds (2), (4), (6), (10) and (13) are higher than that of the compound C-1 because the 3-aminoindazole derivatives of the general formula (II) of this invention have a substituted amino group

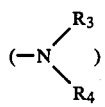

in the ω-position. Further, inhibition values of the compounds (18), (22) and (28) are higher than those of the compounds C-2 and C-3, because the 3-aminoindazole derivatives of the general formula (III) of this invention have a substituted amino group

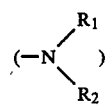

in the ω-position.

In Table 2, there are shown inhibition percentages when the administration amount was varied.

TABLE 2

| Compound No. | Dose (mg/kg) | Inhibition (%) |
|---|---|---|
| (6) | 100 | 67 |
|  | 50 | 53 |
|  | 25 | 40 |
| (22) | 100 | 51 |
|  | 50 | 33 |
|  | 25 | 29 |

TABLE 2-continued

| Compound No. | Dose (mg/kg) | Inhibition (%) |
|---|---|---|
| C-4 | 100 | 51 |
|  | 50 | 20 |
|  | 25 | 8 |
| C-5 | 100 | 55 |
|  | 50 | 18 |
|  | 25 | 15 |

In Table 2, C-4 represents 1-benzyl-3-(3-dimethylaminopropoxy)indazole which is already used as a medicine named benzydamine hydrochloride. C-5 represents 1-phenyl-3-(2-dimethylaminoethylamino)indazole which is a typical compound disclosed in U.S. Pat. No. 3,681,382.

Analgesic activity of 3-aminoindazole derivative hydrochloric acid salts was measured by acetic acid-writhing test. The activity is evaluated with respect to whether the effect of inhibition shows a statistically significant difference (30%). The results of the test are shown in Table 3.

TABLE 3

| 3-Aminoindazole Derivative | Compound No. | Inhibition (%) |
|---|---|---|
| 3-(3-Piperidinopropylamino)indazole | (2) | 53 |
| 3-[3-(2-Methylpiperidino)propylamino]indazole | (6) | 49 |
| 1-(3-Piperidinopropyl)-3-aminoindazole | (18) | 43 |
| 1-[3-(2-Methylpiperidino)propyl]-3-aminoindazole | (22) | 31 |
| 1-Phenyl-3-(3-dimethylaminopropylamino)indazole | C-6 | 0 |
| 1-Phenyl-3-aminoindazole | C-7 | 17 |

In Table 3, 1-phenyl-3-(3-dimethylaminopropylamino)indazole [referred to as "Compound C-6"] and 1-phenyl-3-aminoindazole [referred to as "Compound C-7"] are both comparative compounds. Compound C-6 is a typical compound disclosed in U.S. Pat. No. 3,681,382.

Compounds (6) and (22) of this invention showed potent analgesic activity by the Randall-Selitto test. Analgesic coefficients of the compounds (6), (22) and water (H₂O) are 1.11, 1.05 and 0.8, respectively.

Ulcer inhibition of 3-(3-diethylaminopropylamino)indazole (10) and 1-(3-piperidinopropyl)-3-aminoindazole (18), typical and preferred compounds of this invention, was measured. Gastric ulcer did not occur when 100 mg/kg of the compound (10) or (18) was singly administered at one time. Further, gastric ulcer did not occur, even though the compound (18) was administered for 5 days.

It is well known that the single use of acidic non-steroidal anti-inflammatory drugs causes a side effect in digestive tracts such as gastric ulcer. The inventors found, however, that the side effect could be suppressed if the acidic non-steroidal anti-inflammatory drugs were used in combination with the 3-aminoindazole derivatives or pharmaceutically acceptable salts thereof of this invention. For example, gastric ulcer was caused by a single administration of 10 mg/kg or 20 mg/kg of indomethacin in an ulcer index of 10.2 mm and 34.3 mm, respectively, and in an occurrence frequency of 6/6 (Ulcer generation animal number/Total animal number). However, when 100 mg/kg of compound (18) of this invention was used together with 10 mg/kg of indomethacin, the ulcer index decreased to 2.5 mm though the occurrence frequency was not changed. Further, when 100 mg/kg of compound (10) of this invention was used together with 20 mg/kg of indomethacin the ulcer index decreased to 14.9 mm though the occurrence frequency was not changed.

The toxicity of the 3-aminoindazole derivatives and the pharmaceutically acceptable salts is very low. The acute toxicity ($LD_{50}$) ranged from 50 mg/kg to 700 mg/kg.

The following examples illustrate the present invention in more detail, but they are given for illustrative purposes only and are not to be construed as limiting the invention.

REFERENTIAL EXAMPLE 1

ω-Halogenoalkylamine salts were prepared by the following methods with reference to C. S. Marvel et. al., J. Am. Chem. Soc., 49, 2299 (1927) and H. C. Brill, J. Am. Chem. Soc., 47, 1134 (1925).

1-(2-Bromoethyl)piperidine hydrobromide

In a mixed solution consisting of 50 g of 1,2-dibromoethane, 18.5 g of phenol and 100 ml of water was added dropwise 30 ml of water containing therein 7.9 g of sodium hydroxide at a temperature of 130° C. over 30 minutes with stirring. The reaction solution was further stirred for 6 hours. After completion of the reaction, the organic layer was separated from the reaction solution, washed twice with a saturated aqueous potassium carbonate solution, washed twice with water and dried with anhydrous sodium sulfate. The organic layer was separated by filtration and condensed under reduced pressure to give 34.3 g of 2-phenoxyethyl bromide having a boiling point of 105° C. to 107° C. at 6 mmHg in a yield of 85%.

A mixture of 20 g of 2-phenoxyethyl bromide thus obtained, 7.92 g of piperidine and 12.86 g of potassium carbonate was added into 100 ml of ethyl alcohol and stirred for 6 hours at 100° C. The mixture obtained was filtered and condensed under reduced pressure to give 18.4 g of 1-(2-phenoxyethyl)piperidine having a boiling point of 111° C. to 112° C. at 7 mmHg in a yield of 90%.

15 g of the 1-(2-phenoxyethyl)piperidine thus obtained was reacted with 30 ml of 40% hydrobromic acid at 150° C. for 7 hours with stirring. The reaction solution was cooled, added with 20 ml of chloroform and then the chloroform layer was separated. The hydrobromic acid layer was condensed under reduced pressure and the residue was recrystallized from 5 ml of ethyl alcohol to give 15.1 g of 1-(2-bromoethyl)piperidine hydrobromide having a melting point of 89° C. to 91° C. in a yield of 79%.

Elemental Analysis Value: $C_7H_{15}NBr_2$; Calcd. (%): C 30.80; H 5.54; N 5.13; Br 58.53. Found (%): C 30.71; H 5.68, N 5.01; Br 58.60.

In the same manner as described above were obtained other ω-halogenoalkylamine salts using the reaction conditions as set forth in Tables 4-1, 4-2 and 4-3.

TABLE 4-1

| Run No. | Br(CH$_2$)$_n$Br n | (g) | Phenol (g) | Water (ml) | Aq.NaOH soln. NaOH (g) | Water (ml) | Reaction Temperature (°C.) | Reaction Time (hr) | —O(CH$_2$)$_n$Br Yield [g (%)] |
|---|---|---|---|---|---|---|---|---|---|
| 1 | 3 | 53.7 | 18.5 | 100 | 7.9 | 30 | 130 | 6.5 | 87 |
| 2 | 6 | 64.9 | 18.5 | 100 | 7.9 | 30 | 130 | 6.5 | 78 |
| 3 | 3 | 53.7 | 18.5 | 100 | 7.9 | 30 | 130 | 6.5 | 81 |
| 4 | 3 | 53.7 | 18.5 | 100 | 7.9 | 30 | 130 | 6.5 | 89 |
| 5 | 3 | 53.7 | 18.5 | 100 | 7.9 | 30 | 130 | 6.5 | 85 |
| 6 | 3 | 53.7 | 18.5 | 100 | 7.9 | 30 | 130 | 6.5 | 83 |
| 7 | 3 | 53.7 | 18.5 | 100 | 7.9 | 30 | 130 | 6.5 | 83 |
| 8 | 3 | 53.7 | 18.5 | 100 | 7.9 | 30 | 130 | 6.5 | 87 |
| 9 | 3 | 53.7 | 18.5 | 100 | 7.9 | 30 | 130 | 6.5 | 82 |
| 10 | 3 | 53.7 | 18.5 | 100 | 7.9 | 30 | 130 | 6.5 | 79 |
| 11 | 2 | 50.0 | 18.5 | 100 | 7.9 | 30 | 130 | 6.5 | 80 |
| 12 | 3 | 53.7 | 18.5 | 100 | 7.9 | 30 | 130 | 6.5 | 83 |

TABLE 4-2

| Run No. | —O(CH$_2$)$_n$Br n | (g) | Amine | (g) | Potassium Carbonate (g) | Reaction Medium C$_2$H$_5$OH (ml) | Reaction Temperature (°C.) | Reaction Time (hr) | 1-(n-Phenoxyalkyl)amine | Yield (g) (%) |
|---|---|---|---|---|---|---|---|---|---|---|
| 1 | 3 | 21.40 |  | 7.92 | 12.86 | 100 | 100 | 6 |  | 18.41  89 |

TABLE 4-2-continued

| Run No. | n | ⌬-O(CH$_2$)$_n$Br (g) | Amine | (g) | Potassium Carbonate (g) | Reaction Medium C$_2$H$_5$OH (ml) | Reaction Temperature (°C.) | Reaction Time (hr) | 1-(n-Phenoxyalkyl)amine | Yield (g) | (%) |
|---|---|---|---|---|---|---|---|---|---|---|---|
| 2 | 6 | 25.58 | piperidine (NH) | 7.92 | 12.86 | 100 | 100 | 6 | N(CH$_2$)$_6$O—⌬ | 21.60 | 83 |
| 3 | 3 | 21.40 | pyrrolidine (NH) | 6.62 | 12.86 | 100 | 100 | 6 | N(CH$_2$)$_3$O—⌬ | 18.60 | 91 |
| 4 | 3 | 21.40 | azepane (NH) | 9.22 | 12.86 | 100 | 100 | 6 | N(CH$_2$)$_3$O—⌬ | 19.52 | 84 |
| 5 | 3 | 21.40 | 2-methylpiperidine | 9.22 | 12.86 | 100 | 100 | 6 | CH$_3$—N(CH$_2$)$_3$O—⌬ | 18.82 | 81 |
| 6 | 3 | 21.40 | 2,6-dimethylpiperidine | 10.53 | 12.86 | 100 | 100 | 6 | CH$_3$—N(CH$_2$)$_3$O—⌬—CH$_3$ | 19.95 | 81 |
| 7 | 3 | 21.40 | 4-hydroxypiperidine (HO—NH) | 9.41 | 12.86 | 100 | 100 | 6 | HO—N(CH$_2$)$_3$O—⌬ | 17.11 | 73 |
| 8 | 3 | 21.40 | 4-chloropiperidine (Cl—NH) | 11.12 | 12.86 | 100 | 100 | 6 | Cl—N(CH$_2$)$_3$O—⌬ | 20.56 | 81 |
| 9 | 3 | 21.40 | (C$_2$H$_5$)$_2$NH | 6.80 | 12.86 | 100 | 100 | 6 | (C$_2$H$_5$)$_2$N(CH$_2$)$_3$O—⌬ | 18.58 | 90 |
| 10 | 3 | 21.40 | (C$_4$H$_9$)$_2$NH | 12.02 | 12.86 | 100 | 100 | 6 | (C$_4$H$_9$)$_2$N(CH$_2$)$_3$O—⌬ | 23.35 | 89 |
| 11 | 2 | 20.00 | (CH$_3$)$_2$NH | 4.19 | 12.86 | 100 | 100 | 6 | (CH$_3$)$_2$N(CH$_2$)$_2$O—⌬ | 14.57 | 88 |
| 12 | 3 | 21.40 | CH$_3$N⟨ ⟩NH | 9.32 | 12.86 | 100 | 100 | 6 | CH$_3$N⟨ ⟩N(CH$_2$)$_3$O—⌬ | 21.23 | 91 |

TABLE 4-3

| Run No. | 1-(n-Phenoxyalkyl)amine | 40% Hydrobromic Acid (ml) | Reaction Temperature (°C.) | Reaction Time (hr) | 1-Halogenoalkylamine Salt | Yield (%) | NMR δ (CH₃)₃Si(CH₂)₃-SO₃Na; D₂O | Elemental Analysis Value Calcd. (%) / Found (%) |
|---|---|---|---|---|---|---|---|---|
| 1 | cyclohexyl-N(CH₂)₃O-phenyl, 16.02 g | 30 | 150 | 7 | cyclohexyl-N(CH₂)₃Br·HBr | 71 | 1.77 (m, 6H); 2.37 (m, 2H); 3.33 (m, 6H); 3.57 (t, 2H) | C₈H₁₇NBr₂ — C 33.48/33.31; H 5.97/5.98; N 4.88/4.91; Br 55.67/55.80 |
| 2 | cyclohexyl-N(CH₂)₆O-phenyl, 19.10 g | 30 | 150 | 7 | cyclohexyl-N(CH₂)₆Br·HBr | 73 | 1.64 (m, 14H); 3.35 (m, 6H); 3.59 (t, 2H) | C₁₁H₂₃NBr₂ — C 40.14/40.17; H 7.04/7.25; N 4.26/4.13; Br 48.56/48.45 |
| 3 | cyclopentyl-N(CH₂)₃O-phenyl, 15.00 g | 30 | 150 | 7 | cyclopentyl-N(CH₂)₃Br·HBr | 68 | 2.13 (m, 6H); 3.47 (m, 8H) | C₇H₁₅NBr₂ — C 30.80/30.67; H 5.54/5.31; N 5.13/5.34; Br 58.53/58.68 |
| 4 | cycloheptyl-N(CH₂)₃O-phenyl, 17.05 g | 30 | 150 | 7 | cycloheptyl-N(CH₂)₃Br·HBr | 79 | 1.73 (bs, 8H); 2.35 (m, 2H); 3.34 (m, 6H); 3.53 (t, 2H) | C₉H₁₉NBr₂ — C 35.91/36.08; H 6.36/6.42; N 4.65/4.48; Br 53.08/53.02 |
| 5 | 2-methylcyclohexyl-N(CH₂)₃O-phenyl, 17.05 g | 30 | 150 | 7 | 2-methylcyclohexyl-N(CH₂)₃Br·HBr | 65 | 1.40 (d, 3H); 1.80 (bs, 6H); 2.35 (m, 2H); 3.37 (m, 5H); 3.53 (t, 2H) | C₉H₁₉NBr₂ — C 35.91/35.82; H 6.36/6.27; N 4.65/4.78; Br 53.08/53.13 |
| 6 | 2,6-dimethylcyclohexyl-N(CH₂)₃O-phenyl, 18.07 g | 30 | 150 | 7 | 2,6-dimethylcyclohexyl-N(CH₂)₃Br·HBr | 74 | 1.33 (d, 6H); 1.65 (bs, 8H); 2.23 (m, 2H); 3.45 (m, 4H) | C₁₀H₂₁NBr₂ — C 38.12/38.21; H 6.72/6.85; N 4.45/4.27; Br 50.71/50.67 |
| 7 | 4-hydroxycyclohexyl-N(CH₂)₃O-phenyl, 17.19 g | 30 | 150 | 7 | 4-hydroxycyclohexyl-N(CH₂)₃Br·HBr | 69 | 1.77 (m, 4H); 2.15 (m, 3H); 2.83 (m, 6H); 3.82 (t, 2H) | C₈H₁₇NOBr₂ — C 31.71/31.55; H 5.65/5.72; N 4.62/4.71; Br 52.74/52.55 |

TABLE 4-3-continued

| Run No. | 1-(n-Phenoxyalkyl)amine | (g) | 40% Hydro-bromic Acid (ml) | Reaction Temperature (°C.) | Reaction Time (hr) | 1-Halogenoalkylamine Salt | Yield (%) | NMR δ (CH$_3$)$_3$Si(CH$_2$)$_3$-SO$_3$Na; D$_2$O | Elemental Analysis Value Calcd. (%) Found (%) |
|---|---|---|---|---|---|---|---|---|---|
| 8 | ![structure] Cl-C$_6$H$_{10}$-N(CH$_2$)$_3$O-C$_6$H$_5$ | 18.54 | 30 | 150 | 7 | Cl-C$_6$H$_{10}$-N(CH$_2$)$_3$Br·HBr | 71 | 1.63 (m, 4H) 2.15 (m, 3H) 2.85 (m, 6H) 3.87 (t, 2H) | C$_8$H$_{16}$NClBr$_2$<br>C 29.88  C 29.71<br>H 5.02  H 4.91<br>N 4.36  N 4.63<br>Cl 11.03  Cl 11.31<br>Br 49.71  Br 49.44 |
| 9 | C$_2$H$_5$-N(CH$_2$)$_3$O-C$_6$H$_5$ (C$_2$H$_5$) | 15.15 | 30 | 150 | 7 | C$_2$H$_5$-N(CH$_2$)$_3$Br·HBr (C$_2$H$_5$) | 78 | 1.30 (t, 6H) 2.30 (m, 2H) 3.30 (m, 8H) | C$_7$H$_{17}$NBr$_2$<br>C 30.57  C 30.49<br>H 6.23  H 6.22<br>N 5.09  N 5.23<br>Br 58.11  Br 58.06 |
| 10 | C$_4$H$_9$-N(CH$_2$)$_3$O-C$_6$H$_5$ (C$_4$H$_9$) | 19.25 | 30 | 150 | 7 | C$_4$H$_9$-N(CH$_2$)$_3$Br·HBr (C$_4$H$_9$) | 66 | 1.05 (m, 6H) 1.58 (m, 8H) 2.32 (m, 2H) 3.35 (m, 8H) | C$_{11}$H$_{25}$NBr$_2$<br>C 39.90  C 39.81<br>H 7.61  H 7.55<br>N 4.23  N 4.53<br>Br 48.26  Br 48.11 |
| 11 | CH$_3$-N(CH$_2$)$_2$O-C$_6$H$_5$ (CH$_3$) | 12.07 | 30 | 150 | 7 | CH$_3$-N(CH$_2$)$_2$Br·HBr (CH$_3$) | 78 | 2.93 (s, 6H) 3.70 (bs, 4H) | C$_4$H$_{11}$NBr$_2$<br>C 20.63  C 20.71<br>H 4.76  H 4.83<br>N 6.01  N 5.95<br>Br 68.60  Br 68.51 |
| 12 | CH$_3$N(piperazine)N(CH$_2$)$_3$O-C$_6$H$_5$ | 17.12 | 30 | 150 | 7 | CH$_3$N(piperazine)N(CH$_2$)$_3$Br·2HBr | 71 | 2.37 (m, 2H) 3.03 (s, 3H) 3.73 (m, 12H) | C$_8$H$_{18}$N$_2$Br$_2$<br>C 31.81  C 31.77<br>H 6.01  H 5.98<br>N 9.28  N 9.51<br>Br 52.90  Br 52.74 |

REFERENTIAL EXAMPLE 2

Syntheses of 1-(1-alkyl-3-bromopropyl)piperidine hydrobromides 1-(1-Methyl-3-bromopropyl)piperidine hydrobromide 1-(1-methyl-3-bromopropyl)piperidine hydrobromide was obtained in accordance with the following equations:

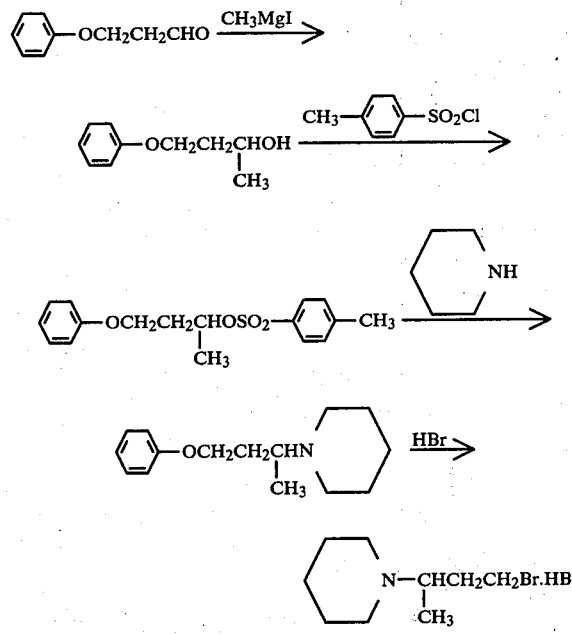

24.9 g of methyl iodide was reacted with 7.26 g of magnesium in 150 ml of anhydrous diethyl ether to obtain methylmagnesium iodide by Grignard reaction. To a solution consisting of 20 g of 3-phenoxypropionaldehyde and 200 ml of anhydrous diethyl ether was added dropwise the methylmagnesium while maintaining a temperature of not more than 20° C. The reaction solution was added with 25 ml of concentrated hydrochloric acid and separated. The ether layer was washed with an aqueous sodium bicarbonate solution, washed with water, dried with anhydrous sodium sulfate and then condensed under reduced pressure to obtain 15.0 g of 4-phenoxy-2-butanol having a boiling point of 61° C. to 62° C. at 3 mmHg in a yield of 67%.

10 g of the 4-phenoxy-2-butanol was reacted with 13.9 g of p-toluenesulfonyl chloride in 21.2 ml of 5N-sodium hydroxide in accordance with the method described in Norris, J. Am. Chem. Soc. 38, 642 (1907) to obtain 18.9 g of 4-phenoxy-2-butyl tosylate having a boiling point of 170° C. to 171° C. at 2 mmHg in a yield of 89%.

In a sealed tube, 10 g of the 4-phenoxy-2-butyl tosylate was reacted with 11.2 g of piperidine in 60 ml of absolute methyl alcohol for one hour at 125° C. After the reaction solution was condensed under reduced pressure. 100 ml of diethyl ether was added into the solution and the solution was separated with 20% aqueous sodium hydroxide solution. After the ether layer was dried with anhydrous sodium sulfate, ether was removed under reduced pressure therefrom. The residue thus obtained was subjected to an alumina-column chromatography using chloroform as the solvent to give 5.46 g of 1-(1-methyl-3-phenoxypropyl)piperidine in a yield of 75%.

5 g of the 1-(1-methyl-3-phenoxypropyl)piperidine thus obtained was reacted with 30 ml of 40% hydrobromic acid at 150° C. for 7 hours with stirring. The reaction solution was cooled, 20 ml of chloroform was added and then the solution separated into two phases, which phases were then separated from each other. The hydrobromic acid was removed under reduced pressure and the residue was recrystallized from 5 ml of ethyl alcohol to give 4.84 g of 1-(1-methyl-3-bromopropyl)-piperidine hydrobromide in a yield of 75%.

Elemental Analysis Value: $C_9H_{19}NBr_2$; Calcd. (%): C 35.91; H 6.36; N 4.65; Br 53.08. Found (%): C 35.95; H 6.31; N 4.81; Br 52.93.

1-(1-Isobutyl-3-bromopropyl)piperidine hydrobromide

The above described procedures were repeated except that 24.0 g of isobutyl bromide was employed instead of 24.9 g of methyl iodide, and then 5.74 g of 1-(1-isobutyl-3-bromopropyl)piperidine hydrobromide was obtained in a yield of 78%.

Elemental Analysis Value: $C_{12}H_{25}NBr_2$; Calcd. (%): C 42.00; H 7.35; N 4.08; Br 46.57. Found (%): C 42.11; H 7.39; N 3.89; Br 46.61.

REFERENTIAL EXAMPLE 3

Syntheses of 1-alkyl-3-bromopropyldiethylamines

1-Methyl-3-bromopropyldiethylamine

1-Methyl-3-bromopropyldiethylamine was prepared in accordance with the following equations:

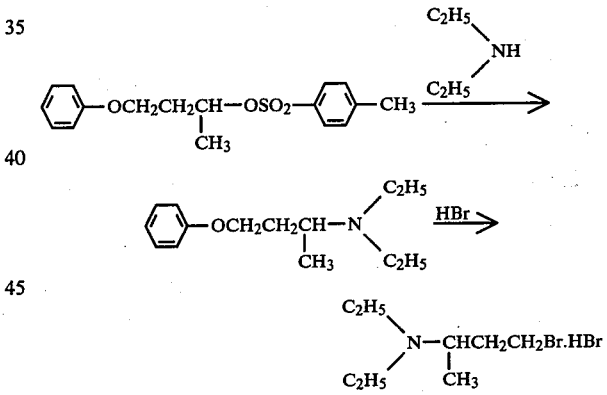

To 60 ml of absolute methyl alcohol were added 10 g of 4-phenoxy-2-butyl tosylate and 9.62 g of diethylamine. The mixture was reacted in a sealed tube for one hour at 125° C. After the reaction solution was condensed under reduced pressure, 100 ml of diethyl ether was added into the solution and the solution was separated with 20% aqueous sodium hydroxide solution. The ether layer was dried with anhydrous sodium sulfate, and the ether was removed under reduced pressure therefrom. The residue thus obtained was subjected to alumina-column chromatography using chloroform as the solvent to give 5.32 g of 1-methyl-3-phenoxypropyl-diethylamine in a yield of 77%.

5 g of the 1-methyl-3-phenoxypropyldiethylamine was reacted with 30 ml of 40% hydrobromic acid at 150° C. for 7 hours with stirring. The reaction solution was cooled, 20 ml of chloroform and was added and then the solution was separated into two phases, which phases were then separated from each other. The hydrobromic acid was removed under reduced pressure and the residue was recrystallized from 5 ml of ethyl alcohol to give 4.88 g of 1-methyl-3-bromopropyldiethylamine hydrobromide in a yield of 78%.

Elemental Analysis Value: $C_8H_{19}NBr_2$; Calcd. (%): C 33.24; H 6.63; N 4.85; Br 55.28. Found (%): C 33.37; H 6.69; N 4.69; Br 55.25.

1-Isobutyl-3-bromopropyldiethylamine hydrobromide

The procedures of obtaining the tosylate as described in Referential Example 2 were repeated except that 24.0 g of isobutyl bromide was employed instead of the 24.9 g of methyl iodide, and 2-methyl-6-phenoxyhexyl tosylate was obtained.

The procedures of preparing 1-methyl-3-bromopropyldiethylamine as described above were repeated except that 11.31 g of 2-methyl-6-phenoxyhexyl tosylate was employed instead of the 10 g of 4-phenoxy-2-butyl tosylate, and 5.33 g of 1-isobutyl-3-bromopropyldiethylamine hydrobromide was obtained in a yield of 75%.

Elemental Analysis Value: $C_{11}H_{25}NBr_2$; Calcd. (%): C 39.90; H 7.61; N 4.23; Br 48.26. Found (%): C 39.89; H 7.83; N 4.10; Br 48.18.

REFERENTIAL EXAMPLE 4

Syntheses of 1-alkyl-3-bromopropyldimethylamines

1-Methyl-3-bromopropyldimethylamine

1-Methyl-3-bromopropyldimethylamine was obtained in accordance with the following equations:

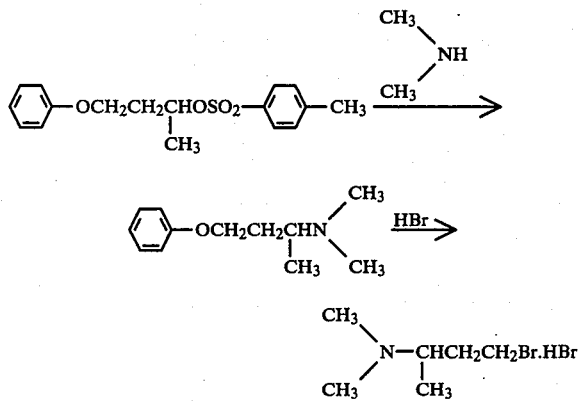

To 60 ml of absolute methyl alcohol were added 10 g of 4-phenoxy-2-butyl tosylate and 5.93 g of dimethylamine. The mixture was reacted in a sealed tube for one hour at 125° C. After the reaction solution was condensed under reduced pressure, 100 ml of diethyl ether was added into the solution and the solution was separated with 20% aqueous sodium hydroxide solution. The ether layer was dried with anhydrous sodium sulfate, and then the ether was removed under reduced pressure therefrom. The residue thus obtained was subjected to an alumina-column chromatography using chloroform as the solvent to give 3.98 g of 1-methyl-3-phenoxypropyldimethylamine in a yield of 66%.

5 g of the 1-methyl-3-phenoxypropyldimethylamine thus obtained was reacted with 30 ml of 40% hydrobromic acid at 150° C. for 7 hours with stirring. The reaction solution was cooled, 20 ml of chloroform was added and then the solution was separated. The hydrobromic acid was removed under reduced pressure and the residue was recrystallized from 5 ml of ethyl alcohol to give 4.46 g of 1-methyl-3-bromopropyldimethylamine hydrobromide in a yield of 79%.

Elemental Analysis Value: $C_6H_{15}NBr_2$; Calcd. (%): C 27.61; H 5.79; N 5.37; Br 61.23. Found (%): C 27.57; H 5.91; N 5.28; Br 61.24.

1-Isobutyl-3-bromopropyldimethylamine hydrobromide

The above described procedures were repeated except that 11.31 g of 2-methyl-6-phenoxyhexyl tosylate obtained in Referential Example 3 was employed instead of the 10 g of 4-phenoxy-2-butyl tosylate, and 5.02 g of 1-isobutyl-3-bromopropyldimethylamine hydrobromide was obtained in a yield of 77%.

Elemental Analysis Value: $C_9H_{21}NBr_2$; Calcd. (%): C 35.67; H 6.98; N 4.62; Br 52.73. Found (%): C 35.91; H 6.71; N 4.66; Br 52.72.

EXAMPLE 1

4.0 g of 3-aminoindazole prepared by the method described in C. E. KWARTLER et. al., J. Am. Chem. Soc., 65, 1804 (1943), 8.18 g of 1-(2-bromoethyl)piperidine hydrobromide obtained from Referential Example 1, 8.28 g of anhydrous potassium carbonate and 80 ml of dried N,N-dimethylformamide were mixed and stirred for 24 hours at 80° C. After the reaction mixture was condensed under reduced pressure, 100 ml of chloroform and 50 ml of water were added to the condensed residue. Then the chloroform layer was separated, dried with anhydrous sodium sulfate and chloroform was removed under reduced pressure. The residue thus obtained was subjected to alumina-column chromatography (alumina: 200 g) using chloroform as the solvent to give 4.09 g of 3-(2-piperidinoethylamino)indazole in a yield of 56%.

IR absorption spectrum ($\nu$ max, cm$^{-1}$): 3310, 3180, 3070, 2948 and 2860.

NMR spectrum [$\delta$, CDCl$_3$]: 1.50 (bs, 6H), 2.47 (bs, 4H), 2.74 (t, 2H), 4.35 (t, 2H), 5.20 (bs, 1H) and 7.05 (m, 4H).

Mass spectrum (m/e, rel. intensity): 244 (M, 100), 245 (M+1, 26), 132 (M−112, 259), 116 (M−128, 428) and 104 (M−140, 969).

In 50 ml of absolute ethyl alcohol was dissolved 4.0 g of 3-(2-piperidinoethylamino)indazole and into the solution was introduced dried hydrogen chloride gas under cooling with ice. Anhydrous diethyl ether was added to the solution to separate crystals. Then the crystals were obtained by filtration and dried to give 3-(2-piperidinoethylamino)indazole hydrochloride.

Elemental Analysis Value: $C_{14}H_{21}N_4Cl$; Calcd. (%): C 59.88; H 7.54; N 19.95; Cl 12.63. Found (%): C 60.01; H 7.61, N 19.90; Cl 12.48.

EXAMPLES 2–16

The same procedures as described in Example 1 were repeated except that 1-halogenoalkylamine salts (a) as set forth in Table 5 were employed instead of 8.18 g of 1-(2-bromoethyl)piperidine hydrobromide. The results and the analytical values of obtained compounds are shown in Tables 5 and 6, respectively.

TABLE 5
| Experimental No. | 1-Halogenoalkylamine Salt (a) | (g) | Product | Form | Yield (%) |
|---|---|---|---|---|---|
| 2 | 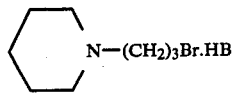 | 8.60 | 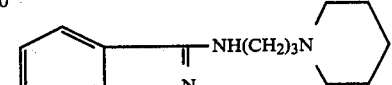 | Solid | 45 |
| 3 | 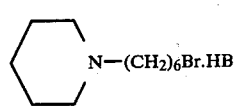 | 9.87 | 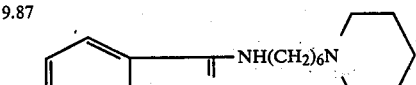 | Solid | 45 |
| 4 | 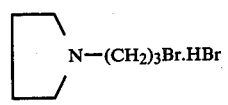 | 8.20 | 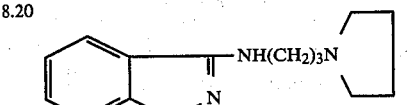 | Solid | 49 |
| 5 | 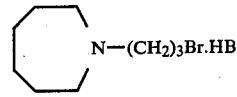 | 9.00 | 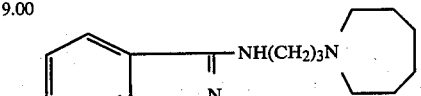 | Solid | 55 |
| 6 | 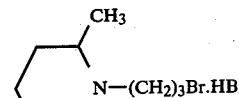 | 9.00 | 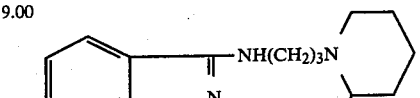 | Solid | 47 |
| 7 | 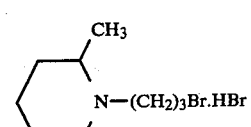 | 9.48 | 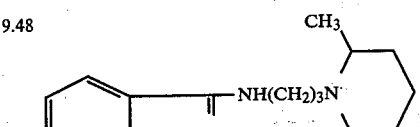 | Solid | 51 |
| 8 | 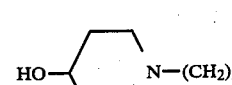 | 9.11 | 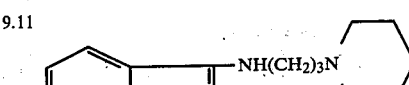 | Oily Substance | 53 |
| 9 | 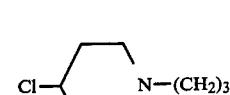 | 9.67 | 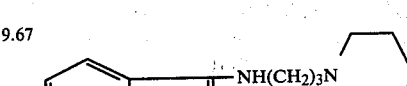 | Solid | 59 |
| 10 | 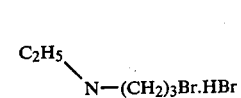 | 8.30 | 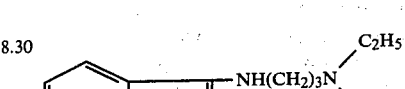 | Solid | 52 |

TABLE 5-continued

| Experimental No. | 1-Halogenoalkylamine Salt (a) | (g) | Product | Form | Yield (%) |
|---|---|---|---|---|---|
| 11 | (C$_4$H$_9$)$_2$N—(CH$_2$)$_3$Br·HBr | 9.89 | 3-[NH(CH$_2$)$_3$N(C$_4$H$_9$)$_2$]-1H-indazole | Solid | 60 |
| 12 | (CH$_3$)$_2$N—(CH$_2$)$_2$Br·HBr | 5.21 | 3-[NH(CH$_2$)$_2$N(CH$_3$)$_2$]-1H-indazole | Solid | 41 |
| 13 | CH$_3$—N(piperazine)N—(CH$_2$)$_3$Br·2HBr | 11.48 | 3-[NH(CH$_2$)$_3$N(piperazine)N—CH$_3$]-1H-indazole | Solid | 51 |
| 14 | piperidine-N—CH(CH$_3$)CH$_2$CH$_2$Br·HBr | 9.00 | 3-[NHCH$_2$CH$_2$CH(CH$_3$)—N(piperidine)]-1H-indazole | Solid | 58 |
| 15 | piperidine-N—CH(CH$_2$CH(CH$_3$)$_2$)CH$_2$CH$_2$Br·HBr | 10.27 | 3-[NHCH$_2$CH$_2$CH(CH$_2$CH(CH$_3$)$_2$)—N(piperidine)]-1H-indazole | Oily Substance | 54 |
| 16 | (C$_2$H$_5$)$_2$N—CH(CH$_3$)CH$_2$CH$_2$Br·HBr | 8.66 | 3-[NHCH$_2$CH$_2$CH(CH$_3$)N(C$_2$H$_5$)$_2$]-1H-indazole | Oily Substance | 61 |

TABLE 6

| Experimental No. | IR Spectrum (cm$^{-1}$) | NMR Spectrum ($\delta$, CDCl$_3$) | Mass Spectrum (m/e) | Elemental Analysis Value Calcd. (%) | Found (%) |
|---|---|---|---|---|---|
| 2 | 3320, 3250, 1608, 1560 | 1.58 (m, 8H), 2.23 (m, 6H), 4.23 (t, 2H), 7.23 (m, 4H) | 258 (M$^+$), 243, 175, 160, 147 | C$_{15}$H$_{23}$N$_4$Cl<br>C 61.11; H 7.86<br>N 19.00; Cl 12.03 | C 61.11; H 7.86<br>N 19.01; Cl 12.02 |
| 3 | 3300, 3180, 3060, 1630, 1550 | 1.40 (bm, 14H), 2.32 (bm, 6H), 4.14 (t, 2H), 7.27 (m, 4H) | 300 (M$^+$), 240, 226, 132, 117 | C$_{18}$H$_{29}$N$_4$Cl<br>C 64.17; H 8.68<br>N 16.63; Cl 10.52 | C 64.25; H 8.77<br>N 16.69; Cl 10.29 |
| 4 | 3310, 3240, 3070, 1610, 1560 | 1.74 (bm, 6H), 2.50 (bm, 6H), 4.33 (t, 2H), 5.33 (bs, 1H), 7.10 (m, 4H) | 244 (M$^+$), 187, 132, 112 | C$_{14}$H$_{21}$N$_4$Cl<br>C 59.88; H 7.54<br>N 19.95; Cl 12.63 | C 59.78; H 7.28<br>N 20.08; Cl 12.86 |
| 5 | 3340, 3210, 3050, 1630, 1550 | 1.53 (bs, 8H), 2.13 (bs, 2H), 2.47 (bs, 6H), 4.20 (t, 2H), 5.60 (bs, 1H), 7.07 (m, 4H) | 272 (M$^+$), 174, 146, 132, 112 | C$_{16}$H$_{25}$N$_4$Cl<br>C 62.22; H 8.16<br>N 18.14; Cl 11.48 | C 62.28; H 8.01<br>N 17.98; Cl 11.73 |
| 6 | 3390, 3200, 3050, 1630, 1560 | 1.00 (d, 3H), 1.57 (bs, 6H), 2.34 (bm, 2H), 2.73 (bm, 5H), 4.20 (t, 2H), 7.33 (m, 5H) | 272 (M$^+$), 174, 146, 132, 112 | C$_{16}$H$_{25}$N$_4$Cl<br>C 62.22; H 8.16<br>N 18.14; Cl 11.48 | C 61.18; H 8.21<br>N 18.31; Cl 12.30 |
| 7 | 3310, 3210, 3030, 1630, 1550 | 1.20 (d, 6H), 1.39 (m, 6H), 2.30 (m, 2H), 2.80 (m, 2H), 3.80 (t, 2H), 4.23 (t, 2H), 7.20 (m, 4H) | 285 (M$^+$), 174, 146, 132, 112 | C$_{17}$H$_{27}$N$_4$Cl<br>C 63.24; H 8.43<br>N 17.35; Cl 10.98 | C 62.99; H 8.61<br>N 17.31; Cl 11.09 |
| 8 | 3400, 3300, 2925, 1630, 1550 | 1.52 (bs, 4H), 2.10 (bm, 3H), 2.98 (m, 6H), 4.23 (t, 2H), 7.20 (m, 4H) | 275 (M$^+$), 175, 146, 132, 112 | C$_{18}$H$_{29}$ON$_4$Cl<br>C 61.26; H 8.28<br>N 15.88; Cl 10.05 | C 61.28; H 8.21<br>N 15.65; Cl 10.17 |
| 9 | 3400, 3310, 2925, 1620 | 1.50 (bs, 4H), 2.11 (bm, 3H), 2.95 (m, 6H), 4.25 (t, 2H) | 292 (M$^+$), 294, 257, 174, 146, 132 | C$_{18}$H$_{28}$N$_4$Cl$_2$<br>C 58.38; H 7.35 | C 58.21; H 7.34 |

TABLE 6-continued

| Experimental No. | IR Spectrum (cm$^{-1}$) | NMR Spectrum (δ,CDCl$_3$) | Mass Spectrum (m/e) | Elemental Analysis Value Calcd. (%) | Found (%) |
|---|---|---|---|---|---|
| 10 | 3310, 3160 2975, 1620 1550 | 7.15 (m, 4H) 0.99 (t, 6H), 2.34 (bm, 4H) 2.47 (q, 4H), 4.27 (t, 2H) 5.06 (bs, 1H), 7.10 (m, 4H) | 246 (M$^+$), 174, 146 132, 112 | N 15.13; Cl 19.14 C$_{14}$H$_{23}$N$_4$Cl C 59.46; H 8.20 N 19.81; Cl 12.53 | N 15.27; Cl 19.18 C 59.39; H 8.15 N 19.99; Cl 12.47 |
| 11 | 3300, 3170 2950, 1620 1550 | 0.95 (m, 6H), 1.28 (m, 10H) 2.30 (m, 6H), 4.24 (t, 2H) 5.17 (bs, 1H), 7.13 (m, 4H) | 302 (M$^+$), 260, 246 146, 132, 112 | C$_{18}$H$_{31}$N$_4$Cl C 63.79; H 9.22 H 16.53; Cl 10.46 | C 63.52; H 9.37 N 16.48; Cl 10.63 |
| 12 | 3320, 3150 2975, 1620 1550 | 2.25 (s, 6H), 2.63 (t, 2H) 4.28 (t, 2H), 5.27 (bs, 1H) 7.07 (m, 4H) | 204 (M$^+$), 133, 71 | C$_{11}$H$_{17}$N$_4$Cl C 54.88; H 7.12 N 23.27; Cl 14.73 | C 54.71; H 7.08 N 23.41; Cl 14.80 |
| 13 | 3300, 3150 2940, 1620 1545 | 2.30 (m, 7H), 2.50 (s, 8H) 4.13 (t, 2H), 7.20 (m, 4H) | 273 (M$^+$), 258, 230 174, 132 | C$_{15}$H$_{25}$N$_5$Cl$_2$ C 52.03; H 7.28 N 20.22; Cl 20.47 | C 52.11; H 7.39 N 20.15; Cl 20.35 |
| 14 | 3315, 3120 2950, 1630 1560 | 0.87 (d, 3H), 1.42 (m, 8H) 2.30 (m, 5H), 4.24 (t, 2H) 5.34 (bs, 1H), 7.10 (m, 4H) | 272 (M$^+$), 257, 240 190, 160, 147, 132 | C$_{16}$H$_{25}$N$_4$Cl C 62.22; H 8.16 N 18.14; Cl 11.48 | C 62.29; H 8.23 N 18.01; Cl 11.47 |
| 15 | 3300, 3150 2960, 1620 1550 | 0.91 (t, 6H), 1.34 (m, 11H) 2.48 (bs, 6H), 4.23 (t, 2H) 7.15 (m, 4H) | 314 (M$^+$), 257, 240 190, 160, 147, 132 | C$_{19}$H$_{31}$N$_4$Cl C 65.03; H 8.90 N 15.97; Cl 10.10 | C 65.01; H 8.79 N 16.13; Cl 10.07 |
| 16 | 3315, 3160 2980, 1620 1560 | 0.93 (m, 9H), 2.31 (m, 3H) 2.48 (q, 4H), 4.23 (t, 2H) 5.30 (bs, 1H), 7.20 (m, 4H) | 260 (M$^+$), 245, 216 187, 173, 160 | C$_{15}$H$_{25}$N$_4$Cl C 70.70; H 9.89 N 5.50; Cl 13.91 | C 70.58; H 10.02 N 5.38; Cl 14.02 |

EXAMPLE 17

5.0 g of the same 3-aminoindazole as Example 1 and 6.68 g of phthalic acid were added to 50 ml of dioxane, and the mixture was stirred for 5 hours at 120° C. The mixture was condensed under reduced pressure, 30 ml of diethyl ether was added and the mixture was stirred under cooling with ice and water for 30 minutes to separate crystals. The crystals were obtained by filtration and dried under reduced pressure to give 8.6 g of 3-phthalimidoindazole in a yield of 87%.

IR absorption spectrum (ν max, cm$^{-1}$): 3310, 1790, 1735 and 1625.

NMR spectrum [δ, (CD$_3$)$_2$SO]: 7.57 (m, 8H) and 13.35 (bs, 1H).

Mass spectrum (m/e, rel. intensity): 263 (M$^+$, 100), 236 (M−27, 17), 219 (M−44, 10), 207 (M−56, 3), 192 (M−71, 5) and 179 (M−84, 5).

To 60 ml of anhydrous N,N-dimethylformamide were added 4.0 g of 3-phthalimidoindazole, 4.76 g of 1-(2-bromoethyl)piperidine hydrobromide as obtained in Referential Example 1 and 6.3 g of anhydrous potassium carbonate and the mixture was stirred for 12 hours at 80° C. After the reaction mixture was cooled, 80 ml of water was added to the mixture and the organic product was extracted with diethyl ether. The ether layer was extracted three times with 2N-hydrochloric acid. Then the hydrochloric acid layer was washed with diethyl ether and the pH of the layer was adjusted to 14 with potassium carbonate. The layer was extracted three times with chloroform. The chloroform layer was dried with anhydrous sodium sulfate and chloroform was removed under reduced pressure to give 3.28 g of 1-(2-piperidinoethyl)-3-phthalimidoindazole in a yield of 57%.

IR absorption spectrum (ν max, cm$^{-1}$): 3050, 2950, 1785, 1730 and 1615.

NMR spectrum [δ, CDCl$_3$]: 1.50 (m, 6H), 2.41 (bs, 4H), 2.78 (t, 2H), 4.45 (t, 2H) and 7.10 (m, 4H).

Mass spectrum (m/e, rel. intensity): 375 (M+1, 100), 291 (M−84, 43), 277 (M−98, 50) and 263 (M−112, 93).

To 70 ml of ethyl alcohol was added 3.23 g of 1-(2-piperidinoethyl)-3-phthalimidoindazole. To the mixture was added 2.5 g of 85% hydrazine under cooling with ice and the mixture was stirred for 3 hours under cooling with ice. The reaction mixture was filtered and the filtrate was condensed under reduced pressure. The condensed residue was added with 20 ml of water and extracted with chloroform. The chloroform layer was extracted with 2N-hydrochloric acid and the pH of the layer was adjusted to 10 with potassium carbonate. The layer was extracted with chloroform. The chloroform layer was dried with anhydrous sodium sulfate and chloroform was removed under reduced pressure to give 1.28 g of 1-(2-piperidinoethyl)-3-aminoindazole in a yield of 66%.

IR absorption spectrum (ν max, cm$^{-1}$): 3315, 3170, 2940, 1640 and 1610.

NMR spectrum [δ, CDCl$_3$]: 1.47 (m, 6H), 2.17 (m, 4H), 2.78 (t, 2H), 4.25 (t, 2H) and 7.20 (m, 4H).

Mass spectrum (m/e, rel. intensity): 244 (M, 100), 160 (M−84, 297), 146 (M−98, 157) and 132 (M−112).

In 15 ml of absolute ethyl alcohol was dissolved 1.28 g of 1-(2-piperidinoethyl)-3-aminoindazole and into the solution was introduced dried hydrogen chloride gas under cooling with ice. Anhydrous diethyl ether was added to the solution to separate crystals. Then the crystals were obtained by filtration and dried to give 1-(2-piperidinoethyl)-3-aminoindazole dihydrochloride.

Elemental Analysis Value: C$_{14}$H$_{22}$N$_4$Cl$_2$; Calcd. (%): C 53.00; H 6.99; N 17.66; Cl 22.35. Found (%): C 52.91; H 6.82; N 17.84; Cl 22.43.

EXAMPLES 18–32

The same procedures as described in Example 17 were repeated except that 1-halogenoalkylamine salts (b) as set forth in Table 7 were employed instead of 4.76 g of 1-(2-bromoethyl)piperidine hydrobromide. The results and the analytical values of obtained compounds are shown in Tables 7 and 8, respectively.

TABLE 7
| Experimental No. | 1-Halogenoalkylamine Salt (b) | (g) | Product | Form | Yield (%) |
|---|---|---|---|---|---|
| 18 | 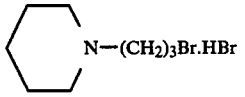 | 5.00 | 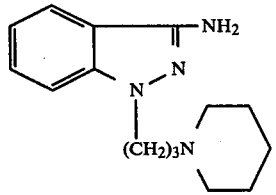 | Solid | 66 |
| 19 | 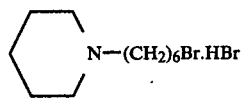 | 5.74 | 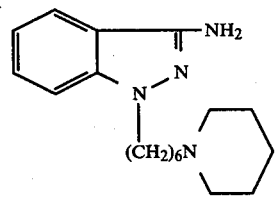 | Solid | 57 |
| 20 | 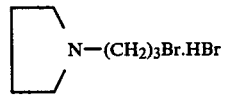 | 4.77 | 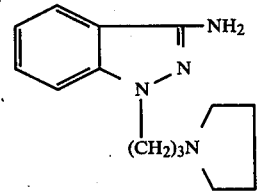 | Solid | 53 |
| 21 | 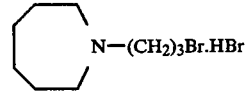 | 5.27 | 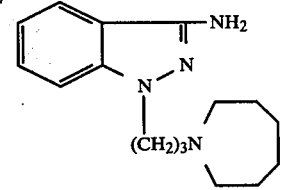 | Solid | 61 |
| 22 | 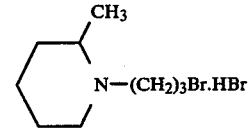 | 5.24 | 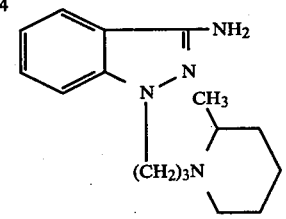 | Solid | 63 |
| 23 | 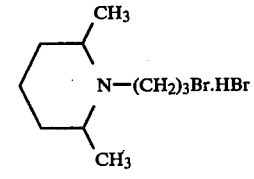 | 5.52 | 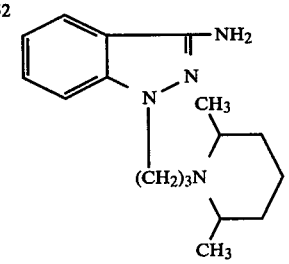 | Solid | 55 |
| 24 | 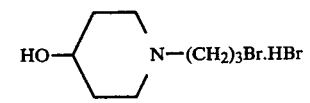 | 5.30 | 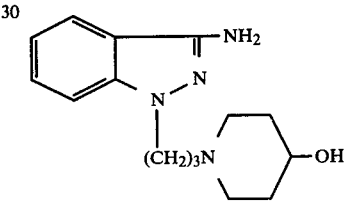 | Oily Substance | 61 |

TABLE 7-continued

| Experimental No. | 1-Halogenoalkylamine Salt (b) | (g) | Product | Form | Yield (%) |
|---|---|---|---|---|---|
| 25 | 4-Cl-piperidine-N—(CH$_2$)$_3$Br·HBr | 5.63 | 3-amino-1-[3-(4-chloropiperidin-1-yl)propyl]-1H-indazole | Solid | 57 |
| 26 | (C$_2$H$_5$)$_2$N—(CH$_2$)$_3$Br·HBr | 4.83 | 3-amino-1-[3-(diethylamino)propyl]-1H-indazole | Solid | 67 |
| 27 | (C$_4$H$_9$)$_2$N—(CH$_2$)$_3$Br·HBr | 5.76 | 3-amino-1-[3-(dibutylamino)propyl]-1H-indazole | Solid | 63 |
| 28 | (CH$_3$)$_2$N—(CH$_2$)$_2$Br·HBr | 3.03 | 3-amino-1-[2-(dimethylamino)ethyl]-1H-indazole | Solid | 68 |
| 29 | piperidine-N—CH(CH$_3$)CH$_2$CH$_2$Br·HBr | 5.24 | 3-amino-1-[3-(piperidin-1-yl)butyl]-1H-indazole | Solid | 59 |
| 30 | piperidine-N—CH(CH$_2$CH(CH$_3$)$_2$)CH$_2$CH$_2$Br·HBr | 5.98 | corresponding indazole | Oily Substance | 60 |
| 31 | (CH$_3$)$_2$N—CH(CH$_2$CH(CH$_3$)$_2$)CH$_2$CH$_2$Br·HBr | 5.26 | corresponding indazole | Oily Substance | 51 |

TABLE 7-continued

| Experimental No. | 1-Halogenoalkylamine Salt (b) | (g) | Product | Form | Yield (%) |
|---|---|---|---|---|---|
| 32 | CH$_3$—N(piperazine)N—(CH$_2$)$_3$Br.2HBr | 4.98 | 3-amino-1-[3-(4-methylpiperazin-1-yl)propyl]indazole | Solid | 58 |

TABLE 8

| Experimental No. | IR Spectrum (cm$^{-1}$) | NMR Spectrum (δ, CDCl$_3$) | Mass Spectrum (m/e) | Elemental Analysis Value Calcd. (%) | Found (%) |
|---|---|---|---|---|---|
| 18 | 3310, 3180 2940, 1645 1615 | 1.43 (m, 6H), 2.17 (m, 8H) 4.25 (m, 4H), 7.20 (m, 4H) | 258 (M$^+$), 173, 160 146 | C$_{15}$H$_{24}$N$_4$Cl$_2$ C 54.38; H 7.30 N 16.91; Cl 21.41 | C 54.42; H 7.42 N 17.05; Cl 21.11 |
| 19 | 3320, 3200 2950, 1650 1610 | 1.39 (m, 14H), 2.29 (bm, 6H) 4.10 (t, 2H), 4.30 (bs, 2H) 7.25 (m, 4H) | 300 (M$^+$), 216, 202 188, 174 | C$_{18}$H$_{30}$N$_4$Cl$_2$ C 57.90; H 8.10 N 15.01; Cl 18.99 | C 58.01; H 8.17 N 14.87; Cl 18.95 |
| 20 | 3300, 3190 2950, 1645 1610 | 1.70 (bm, 6H), 2.48 (bm, 6H) 4.25 (t, 2H), 4.70 (bs, 2H) 7.25 (m, 4H) | 244 (M$^+$), 174, 160 146 | C$_{14}$H$_{22}$N$_4$Cl$_2$ C 53.00; H 6.99 H 17.66; Cl 22.35 | C 52.81; H 6.97 N 17.83, Cl 22.39 |
| 21 | 3310, 3170 2950, 1640 1610 | 1.52 (bs, 8H), 2.10 (bs, 2H) 2.47 (bs, 6H), 4.20 (t, 2H) 4.68 (bs, 2H), 7.10 (m, 4H) | 272 (M$^+$), 174, 160 146 | C$_{16}$H$_{26}$N$_4$Cl$_2$ C 55.65; H 7.59 N 16.22; Cl 20.54 | C 55.81; H 7.61 N 15.98; Cl 20.60 |
| 22 | 3320, 3210 2930, 2860 2790, 1615 1580 | 0.90 (d, 3H), 1.50 (m, 6H) 2.32 (m, 7H), 4.00 (bs, 2H) 4.11 (t, 2H), 7.18 (m, 4H) | 272 (M$^+$), 258, 176 161, 147, 133 | C$_{16}$H$_{26}$N$_4$Cl$_2$ C 55.65; H 7.59 N 16.22; Cl 20.54 | C 55.48; H 7.41 N 16.41; Cl 20.70 |
| 23 | 3300, 3230 2940, 2850 1630, 1605 | 1.19 (d, 6H), 1.39 (m, 6H) 2.30 (m, 2H), 2.80 (m, 2H) 3.75 (t, 2H), 4.20 (t, 2H) 4.50 (bs, 2H), 7.23 (m, 4H) | 286 (M$^+$), 271, 256 174, 160, 146 | C$_{17}$H$_{28}$N$_4$Cl$_2$ C 56.83; H 7.85 N 15.59; Cl 19.73 | C 57.07; H 7.91 N 15.35; Cl 19.67 |
| 24 | 3400, 3300 2950, 1630 1570 | 1.48 (bs, 4H), 2.08 (bm, 3H) 2.90 (m, 6H), 4.19 (t, 2H) 4.90 (bs, 2H), 7.21 (m, 4H) | 275 (M$^+$), 258, 174 160, 146 | C$_{18}$H$_{30}$ON$_4$Cl$_2$ C 55.52; H 7.77 N 14.39; Cl 18.21 | C 55.38; H 7.65 N 14.58; Cl 22.39 |
| 25 | 3350, 3250 2950, 2860 1625, 1600 | 1.45 (bs, 4H), 2.09 (bm, 3H) 2.89 (bm, 6H), 4.23 (t, 2H) 4.47 (bs, 2H), 7.20 (m, 4H) | 292 (M$^+$), 257, 174 160, 146 | C$_{18}$H$_{29}$N$_4$Cl$_3$ C 53.01; H 7.17 N 13.74; Cl 26.08 | C 52.95; H 7.03 N 13.95; Cl 26.07 |
| 26 | 3320, 3220 2930, 2850 1615, 1580 | 0.97 (t, 6H), 2.34 (bm, 4H) 2.47 (q, 4H), 4.25 (t, 2H) 5.00 (bs, 2H), 7.11 (m, 4H) | 246 (M$^+$), 217, 188 174, 160, 146 | C$_{14}$H$_{24}$N$_4$Cl$_2$ C 52.67; H 7.57 N 17.55; Cl 22.21 | C 52.51; H 7.52 N 17.73; Cl 22.24 |
| 27 | 3300, 3210 3010, 2960 1650, 1600 1560 | 0.92 (m, 6H), 1.28 (m, 10H) 2.30 (m, 6H), 4.20 (t, 2H) 4.51 (bs, 2H), 7.10 (m, 2H) | 302 (M$^+$), 245, 188 174, 160, 146 | C$_{18}$H$_{32}$N$_4$Cl$_2$ C 57.59; H 8.59 N 14.93; Cl 18.89 | C 57.61; H 8.73 N 14.73, Cl 18.93 |
| 28 | 3320, 3200 3050, 2970 1660, 1610 1575 | 2.20 (s, 6H), 2.67 (t, 2H) 4.17 (t, 2H), 4.85 (bs, 2H) 7.27 (m, 4H) | 204 (M$^+$), 177, 147 133 | C$_{11}$H$_{18}$N$_4$Cl$_2$ C 47.66; H 6.54 N 20.22; Cl 25.58 | C 47.53; H 6.41 N 20.41; Cl 25.65 |
| 29 | 3310, 3170 2950, 1630 1600, 1560 | 0.85 (d, 3H), 1.41 (m, 8H) 2.30 (m, 5H), 4.20 (t, 2H) 4.70 (bs, 2H), 7.15 (m, 4H) | 272 (M$^+$), 257, 173 160, 146 | C$_{16}$H$_{26}$N$_4$Cl$_2$ C 55.65; H 7.59 N 16.22; Cl 20.54 | C 55.71; H 7.63 N 16.03; Cl 20.63 |
| 30 | 3300, 3160 2960, 1620 1600, 1550 | 0.90 (d, 6H), 1.34 (m, 11H) 2.48 (bs, 6H), 4.20 (t, 2H) 4.79 (bs, 2H), 7.22 (m, 4H) | 314 (M$^+$), 257, 173 160, 146 | C$_{19}$H$_{32}$N$_4$Cl$_2$ C 58.91; H 8.33 N 14.46; Cl 18.30 | C 59.04; H 8.37 N 14.22; Cl 18.37 |
| 31 | 3300, 3180 2950, 1630 1560 | 0.92 (t, 6H), 1.33 (m, 5H) 2.19 (m, 7H), 4.15 (t, 2H) 4.98 (bs, 2H), 7.20 (m, 4H) | 274 (M$^+$), 217, 202 187, 173, 160 | C$_{16}$H$_{28}$N$_4$Cl$_2$ C 55.33; H 8.13 N 16.13; Cl 20.41 | C 55.21; H 8.00 N 16.37; Cl 20.42 |
| 32 | 3320, 3210 2940, 2800 1710, 1615 | 2.32 (m, 15H), 4.15 (t, 2H) 4.68 (bs, 2H), 7.33 (m, 4H) | 273 (M$^+$), 258, 243 187, 173, 160 | C$_{15}$H$_{26}$N$_5$Cl$_3$ C 47.07; H 6.85 N 18.30; Cl 27.78 | C 47.21; H 6.89 N 18.02; Cl 27.88 |

EXAMPLE 33

To 60 ml of anhydrous N,N-dimethylformamide were added 4.00 g of 1-(3-diethylaminopropyl)-3-aminoindazole prepared by the same method as Example 26, 8.98 g of 3-bromopropyldiethylamine hydrobromide and 7.89 g of anhydrous potassium carbonate, and the mixture was stirred for 12 hours at 80° C. After cooling the reaction mixture, the mixture was added with 80 ml of water and extracted with diethyl ether. Then the ether layer was extracted three times with 2N-hydrochloric acid. The hydrochloric acid layer was washed with diethyl ether and the pH of the layer was adjusted to 14 with potassium carbonate. The layer was extracted three times with chloroform. The chloroform layer was dried with anhydrous sodium sulfate and chloroform was removed under reduced pressure. The residue thus obtained was subjected to an alumina-column chromatography (alumina: 200 g) using chloroform as the solvent to give 3.05 g of 1-(diethylaminopropyl)-3-(3-diethylaminopropylamino)indazole in a yield of 52%.

IR absorption spectrum ($\nu$ max, cm$^{-1}$): 3305, 3200, 2980, 2800 and 1615.

NMR spectrum [$\delta$, CDCl$_3$]: 0.93 (t, 12H), 1.97 (m, 4H), 2.50 (m, 8H), 4.13 (t, 4H) and 7.27 (m, 4H).

Mass spectrum (m/e, rel. intensity): 359 (M$^+$, 100), 360 (M+1, 39), 330 (M−29, 37), 301 (M−58, 21), 260 (M−99, 104) and 246 (M−113, 185).

In 50 ml of absolute ethyl alcohol was dissolved 3.0 g of 1-(3-diethylaminopropyl)-3-(3-diethylamino-propylamino)indazole and into the solution was introduced dried hydrogen chloride gas under cooling with ice. Anhydrous diethyl ether was added to the solution to separate crystals. Then the crystals were obtained by filtration and dried to give 1-(3-diethylaminopropyl)-3-(3-diethylaminopropylamino)indazole dihydrochloride.

Elemental Analysis Value: $C_{21}H_{39}N_5Cl_2$; Calcd. (%): C 58.32; H 9.09; N 16.19; Cl 16.40. Found (%): C 58.21; H 8.98; N 16.30; Cl 16.51.

EXAMPLES 34–37

The same procedures as described in Example 33 were repeated except that 1-halogenoalkylamine salts (c) as set forth in Table 9 were employed instead of 8.98 g of 3-bromopropyldiethylamine hydrobromide. The results and the analytical values of the compounds obtained are shown in Tables 9 and 10, respectively.

TABLE 9

| Experimental No. | 1-Halogenoalkylamine Salt (c) | (g) | Product | Form | Yield (%) |
|---|---|---|---|---|---|
| 34 | piperidine-N—(CH$_2$)$_3$Br·HBr | 9.30 | indazole with NH(CH$_2$)$_3$N-piperidine, N-(CH$_2$)$_3$N(C$_2$H$_5$)$_2$ | Oily Substance | 54 |
| 35 | piperidine-N—(CH$_2$)$_6$Br·HBr | 10.68 | indazole with NH(CH$_2$)$_6$N-piperidine, N-(CH$_2$)$_3$N(C$_2$H$_5$)$_2$ | Oily Substance | 47 |
| 36 | (C$_4$H$_9$)$_2$N—(CH$_2$)$_3$Br·HBr | 10.70 | indazole with NH(CH$_2$)$_3$N(C$_4$H$_9$)$_2$, N-(CH$_2$)$_3$N(C$_2$H$_5$)$_2$ | Oily Substance | 57 |
| 37 | piperidine-N—CHCH$_2$CH$_2$Br·HBr (CH$_3$) | 9.74 | indazole with NHCH$_2$CH$_2$CHN-piperidine (CH$_3$), N-(CH$_2$)$_3$N(C$_2$H$_5$)$_2$ | Oily Substance | 55 |

TABLE 10

| Experimental No. | IR Spectrum (cm$^{-1}$) | NMR Spectrum ($\delta$, CDCl$_3$) | Mass Spectrum (m/e) | Elemental Analysis Value Calcd. (%) | Found (%) |
|---|---|---|---|---|---|
| 34 | 3300, 3210 2970, 2810 1610 | 0.96 (t, 6H), 1.51 (m, 8H) 2.30 (m, 10H), 2.47 (q, 4H) 4.21 (t, 4H), 7.21 (m, 4H) | 372 (M$^+$), 343, 314 258, 174 | $C_{22}H_{39}N_5Cl_2$ C 59.45; H 8.84 N 15.76; Cl 15.95 | C 59.31; H 8.77 N 15.89; Cl 16.03 |
| 35 | 3310, 3210 2960, 2800 1615 | 0.98 (t, 6H), 1.39 (bm, 14H) 2.32 (m, 10H), 2.49 (q, 4H) 4.20 (t, 4H), 7.25 (m, 4H) | 414 (M+), 385, 356 300, 216 | $C_{25}H_{45}N_5Cl_2$ C 61.71; H 9.32 N 14.39; Cl 14.58 | C 61.93; H 9.35 N 14.07; Cl 14.65 |

TABLE 10-continued

| Experimental No. | IR Spectrum (cm$^{-1}$) | NMR Spectrum ($\delta$, CDCl$_3$) | Mass Spectrum (m/e) | Elemental Analysis Value Calcd. (%) | Found (%) |
|---|---|---|---|---|---|
| 36 | 3320, 3200 | 0.96 (m, 12H), 1.28 (m, 10H) | 416 (M$^+$), 387, 358 | C$_{25}$H$_{47}$N$_5$Cl$_2$ | |
| | 2950, 2815 | 2.30 (m, 10H), 2.48 (q, 4H) | 302, 245 | C 61.46; H 9.70 | C 61.30; H 9.68 |
| | 1620 | 4.10 (t, 4H), 7.17 (m, 4H) | | N 14.33; Cl 14.51 | N 14.41; Cl 14.61 |
| 37 | 3300, 3230 | 0.90 (m, 9H), 1.40 (m, 8H) | 386 (M$^+$), 357, 328 | C$_{23}$H$_{41}$N$_5$Cl$_2$ | |
| | 2980, 2800 | 2.29 (m, 9H), 2.49 (q, 4H) | 272, 188 | C 60.25; H 9.01 | C 60.38; H 9.09 |
| | 1610 | 4.15 (t, 4H), 7.20 (m, 4H) | | N 15.27; Cl 15.47 | N 15.01; Cl 15.52 |

EXAMPLE 38

The same procedures as described in Example 33 were repeated except that 4.20 g of 1-(3-piperidinopropyl)-3-aminoindazole prepared by the same method as Example 18 was employed instead of 4.00 g of 1-(3-diethylaminopropyl)-3-aminoindazole. The results and the analytical values of the compound obtained are shown in Tables 11 and 12, respectively.

TABLE 11

| Experimental No. | 1-Halogenoalkylamine Salt (d) | (g) | Product | Form | Yield (%) |
|---|---|---|---|---|---|
| 38 | (C$_2$H$_5$)$_2$N—(CH$_2$)$_3$Br·HBr | 8.98 | indazole-NH(CH$_2$)$_3$—N(C$_2$H$_5$)$_2$, N1-(CH$_2$)$_3$N(piperidino) | Oily Substance | 53 |
| 39 | piperidino-N—(CH$_2$)$_3$Br·HBr | 9.30 | indazole-NH(CH$_2$)$_3$—N(piperidino), N1-(CH$_2$)$_3$N(piperidino) | Oily Substance | 59 |
| 40 | piperidino-N—(CH$_2$)$_6$Br·HBr | 10.68 | indazole-NH(CH$_2$)$_6$—N(piperidino), N1-(CH$_2$)$_3$N(piperidino) | Oily Substance | 49 |
| 41 | piperidino-N—CH(CH$_3$)CH$_2$CH$_2$Br·HBr | 9.74 | indazole-NHCH$_2$CH$_2$CH(CH$_3$)—N(piperidino), N1-(CH$_2$)$_3$N(piperidino) | Oily Substance | 51 |

TABLE 12

| Experimental No. | IR Spectrum (cm$^{-1}$) | NMR Spectrum ($\delta$, CDCl$_3$) | Mass Spectrum (m/e) | Elemental Analysis Value Calcd. (%) | Found (%) |
|---|---|---|---|---|---|
| 38 | 3320, 3210 | 0.97 (t, 6H), 1.49 (m, 8H) | 372 (M$^+$, 100), 343 | C$_{22}$H$_{39}$N$_5$Cl$_2$ | |
| | 2960, 2820 | 2.32 (m, 10H), 2.41 (q, 4H) | (M-29, 61) 314 (M-58, | C 59.45; H 8.84 | C 59.61; H 8.95 |
| | 1615 | 4.15 (t, 4H), 7.20 (m, 4H) | 79), 258 (M-114, 132) 174 (M-198, 140) | N 15.76; Cl 15.95 | N 15.42; Cl 16.02 |
| 39 | 3330, 3210 | 1.56 (m, 16H), 2.20 (m, 12H) | 384 (M$^+$), 370, 356 | C$_{23}$H$_{39}$N$_5$Cl$_2$ | |

TABLE 12-continued

| Experimental No. | IR Spectrum (cm$^{-1}$) | NMR Spectrum ($\delta$,CDCl$_3$) | Mass Spectrum (m/e) | Elemental Analysis Value Calcd. (%) | Found (%) |
|---|---|---|---|---|---|
|  | 2960, 2820, 1615 | 4.20 (t, 4H), 7.20 (m, 4H) | 342, 328 | C 60.52; H 8.61  N 15.34; Cl 15.53 | C 60.43; H 8.52  N 15.51; Cl 15.54 |
| 40 | 3300, 3210, 2980, 2820, 1610 | 1.41 (m, 20H), 2.30 (m, 14H)  4.17 (t, 4H), 7.20 (m, 4H) | 426 (M+), 412, 398  384, 370, 356 | C$_{26}$H$_{45}$N$_5$Cl$_2$  C 62.63; H 9.10  N 14.05; Cl 14.22 | C 62.79; H 9.21  H 13.89; Cl 14.11 |
| 41 | 3310, 3200, 2970, 2810, 1620 | 0.88 (d, 3H), 1.40 (m, 14H)  2.20 (m, 13H), 4.25 (t, 4H)  7.17 (m, 4H) | 398 (M+), 384, 370  356, 342, 328 | C$_{24}$H$_{41}$N$_5$Cl$_2$  C 61.27; H 8.78  N 14.88; Cl 15.07 | C 61.35; H 8.81  N 14.67; Cl 15.17 |

EXAMPLES 39-41

The same procedures as described in Example 38 were repeated except that 1-halogenoalkylamine salts (d) as set forth in Table 11 were employed instead of 8.98 g of 3-bromopropyldiethylamine hydrobromide. The results and the analytical values of the compounds obtained are also shown in Tables 11 and 12, respectively.

EXAMPLE 42

The same procedures as described in Example 33 were repeated except that 4.40 g of 1-(3-piperidinobutyl)-3-aminoindazole prepared by the same method as Example 29 and 8.07 g of 3-bromopropyldimethylamine hydrobromide were employed instead of 4.00 g of 1-(3-diethylaminopropyl)-3-aminoindazole and 8.98 g of 3-bromopropyldiethylamine hydrobromide, respectively. The results and the analytical values of the compound obtained are shown in Tables 13 and 14, respectively.

TABLE 13

| Experimental No. | 1-Halogenoalkylamine Salt (e) | (g) | Product | Form | Yield (%) |
|---|---|---|---|---|---|
| 42 | (CH$_3$)$_2$N—(CH$_2$)$_3$Br·HBr | 8.07 | [indazole derivative with NH(CH$_2$)$_3$N(CH$_3$)$_2$ and N-(CH$_2$)$_2$CHN(piperidino)CH$_3$] | Oily Substance | 51 |
| 43 | piperidino-N—(CH$_2$)$_3$Br·HBr | 9.30 | [indazole derivative with NH(CH$_2$)$_3$-N(piperidino) and N-(CH$_2$)$_2$CHN(piperidino)CH$_3$] | Oily Substance | 48 |
| 44 | piperidino-N—CH(CH$_2$CH(CH$_3$)$_2$)CH$_2$CH$_2$Br·HBr | 11.11 | [indazole derivative with NHCH$_2$CH$_2$CH—N(piperidino) side chain and N-(CH$_2$)$_2$CHN(piperidino)CH$_3$] | Oily Substance | 51 |
| 45 | (CH$_3$)$_2$N—CHCH$_2$CH$_2$Br·HBr (with CH$_3$) | 8.46 | [indazole derivative with NHCH$_2$CH$_2$CHN(CH$_3$)$_2$CH$_3$ and N-(CH$_2$)$_2$CHN(piperidino)CH$_3$] | Oily Substance | 45 |

TABLE 14

| Experimental No. | IR Spectrum (cm⁻) | NMR Spectrum (δ,CDCl₃) | Mass Spectrum (m/e) | Elemental Analysis Value Cald. (%) | Found (%) |
|---|---|---|---|---|---|
| 42 | 3330, 3200 | 0.89 (m, 9H), 1.40 (m, 8H) | 386 (M⁺, 100), 357 (M- | $C_{23}H_{41}N_5Cl_2$ | |
| | 2970, 2830 | 2.30 (m, 9H), 2.46 (q, 4H) | 29, 51), 328 (M-58, 33), | C 60.25; H 9.01 | C 60.01; H 9.37 |
| | 1610 | 4.19 (t, 4H), 7.25 (m, 4H) | 272 (M-114, 108), 188 (M-198, 113) | N 15.27; Cl 15.47 | N 15.43; Cl 15.19 |
| 43 | 3310, 3210 | 0.90 (d, 3H), 1.41 (m, 14H) | 398 (M⁺), 384, 370 | $C_{24}H_{41}N_5Cl_2$ | |
| | 2980, 2810 | 2.22(m, 13H), 4.20 (t, 4H) | 356, 342, 328 | C 61.27; H 8.78 | C 60.98; H 8.99 |
| | 1615 | 7.20 (m, 4H) | | N 14.88; Cl 15.07 | N 14.87; Cl 15.16 |
| 44 | 3330, 3200 | 0.92 (m, 9H), 1.47 (m, 19H) | 454 (M⁺), 439, 424 | $C_{28}H_{49}N_5Cl_2$ | |
| | 2960, 2830 | 2.25 (m, 10H), 4.29 (t, 4H) | 409, 395, 311, 227 | C 63.86; H 9.38 | C 63.59; H 9.55 |
| | 1620 | 7.25 (m, 4H) | | N 13.30; Cl 13.46 | N 13.48; Cl 13.38 |
| 45 | 3320, 3230 | 0.93 (m, 6H), 1.35 (m, 10H) | 372 (M⁺), 357, 342 | $C_{22}H_{39}N_5Cl_2$ | |
| | 2970, 2840 | 2.31 (m, 12H), 4.17 (t, 4H) | 327, 243, 229 | C 59.45; H 8.84 | C 59.23; H 8.99 |
| | 1625 | 7.17 (m, 4H) | | N 15.76; Cl 15.95 | N 15.95; Cl 15.83 |

EXAMPLES 43–45

The same procedures as described in Example 42 were repeated except that 1-halogenoalkylamine salts (e) as set forth in Table 13 were employed instead of 8.07 g of 3-bromopropyldimethylamine hydrobromide. The results and the analytical values of the compounds obtained are also shown in Tables 13 and 14, respectively.

EXAMPLE 46

The same procedures as described in Example 33 were repeated except that 3.75 g of 1-(3-dimethylaminobutyl)-3-aminoindazole was employed instead of 4.00 g of 1-(3-diethylaminopropyl)-3-aminoindazole. The results and the analytical values of the compound obtained are shown in Tables 15 and 16, respectively.

TABLE 15

| Experimental No. | 1-Halogenoalkylamine Salt (f) | (g) | Product | Form | Yield (%) |
|---|---|---|---|---|---|
| 46 | $C_2H_5$—N(—$C_2H_5$)—(CH₂)₃Br·HBr | 8.98 | [indazole derivative with NH(CH₂)₃—N(C₂H₅)₂ and (CH₂)CHN(CH₃)₂ with CH₃ substituent] | Oily Substance | 57 |
| 47 | piperidinyl—(CH₂)₃Br·HBr | 9.30 | [indazole derivative with NH(CH₂)₃—N(piperidinyl), (CH₂)₂CHN(CH₃)₂] | Oily Substance | 44 |
| 48 | piperidinyl—CH(CH₃)CH₂CH₂Br·HBr | 9.74 | [indazole derivative with NHCH₂CH₂CH(CH₃)—N(piperidinyl), (CH₂)₂CHN(CH₃)₂] | Oily Substance | 48 |

TABLE 15-continued

| Experimental No. | 1-Halogenoalkylamine Salt (f) | (g) | Product | Form | Yield (%) |
|---|---|---|---|---|---|
| 49 | $C_2H_5$-N-CHCH$_2$CH$_2$Br·HBr, with $C_2H_5$, CH$_2$, CH(CH$_3$)$_2$ | 10.73 | Indazole derivative with $C_2H_5$, NHCH$_2$CH$_2$CHN($C_2H_5$)($C_2H_5$), N-(CH$_2$)$_2$CHN(CH$_3$)(CH$_3$), CH$_2$CH($C_2H_5$)($C_2H_5$) | Oily Substance | 42 |

TABLE 16

| Experimental No. | IR Spectrum (cm$^{-1}$) | NMR Spectrum ($\delta$, CDCl$_3$) | Mass Spectrum (m/e) | Elemental Analysis Value Calcd. (%) | Found (%) |
|---|---|---|---|---|---|
| 46 | 3310, 3200 2950, 2810 1620 | 0.95 (m, 9H), 2.30 (m, 13H) 2.46 (q, 4H), 4.17 (t, 4H) 7.15 (m, 4H) | 346 (M$^+$, 100), 317 (M-29, 76), 288 (M-58, 49), 274 (M-72, 110), 260 (M-96, 130) | $C_{20}H_{37}N_5Cl_2$ C 57.41; H 8.91 N 16.74; Cl 16.94 | C 57.27; H 9.08 N 16.77; Cl 16.88 |
| 47 | 3330, 3210 2990, 2850 1620 | 0.90 (d, 3H), 1.58 (m, 10H) 2.24 (m, 13H), 4.17 (t, 4H) 7.20 (m, 4H) | 358 (M$^+$), 343, 328 314, 299 | $C_{21}H_{37}N_5Cl_2$ C 58.60; H 8.66 N 16.27; Cl 16.47 | C 58.42; H 8.73 N 16.30; Cl 16.55 |
| 48 | 3300, 3230 2970, 2830 1610 | 0.93 (m, 6H), 1.55 (m, 10H) 2.30 (m, 12H), 4.20 (t, 4H) 7.15 (m, 4H) | 372 (M$^+$), 357, 342 328, 313 | $C_{22}H_{39}N_5Cl_2$ C 59.45; H 8.84 N 15.76; Cl 15.95 | C 59.22; H 9.01 N 15.63; Cl 16.14 |
| 49 | 3310, 3210 2980, 2830 1610 | 0.95 (m, 15H), 1.50 (m, 7H) 2.25 (m, 12H), 4.20 (t, 4H) 7.17 (m, 4H) | 402 (M$^+$), 387, 372 358, 343 | $C_{24}H_{45}N_5Cl_2$ C 60.74; H 9.56 N 14.76; Cl 14.94 | C 60.51; H 9.77 N 14.89; Cl 14.83 |

EXAMPLES 47–49

The same procedures as described in Example 46 were repeated except that 1-halogenoalkylamine salts (f) as set forth in Table 15 were employed instead of 8.98 g. of 3-bromopropyldiethylamine hydrobromide. The results and the analytical values of the compounds obtained are also shown in Tables 15 and 16, respectively.

THERAPEUTIC EXAMPLE 1

The anti-inflammatory activity of the 3-aminoindazole derivative hydrochloric acid salts obtained by Examples 1–49 of this invention was measured by the standard method of carrageenin edema test. In these tests, the amount of the administration of the salts was 100 mg/kg. The results are shown in Table 17 (Inhibition (%) was measured three hours after the injection).

TABLE 17

| Example No. | Inhibition (%) | Example No. | Inhibition (%) |
|---|---|---|---|
| 1 | 48 | 26 | 61 |
| 2 | 55 | 27 | 57 |
| 3 | 30 | 28 | 44 |
| 4 | 30 | 29 | 46 |
| 5 | 59 | 30 | 35 |
| 6 | 67 | 31 | 28 |
| 7 | 35 | 32 | 27 |
| 8 | 47 | 33 | 29 |
| 9 | 68 | 34 | 28 |
| 10 | 66 | 35 | 21 |
| 11 | 65 | 36 | 31 |
| 12 | 52 | 37 | 27 |
| 13 | 30 | 38 | 29 |
| 14 | 55 | 39 | 28 |
| 15 | 42 | 40 | 21 |
| 16 | 63 | 41 | 28 |
| 17 | 47 | 42 | 29 |
| 18 | 54 | 43 | 28 |
| 19 | 29 | 44 | 21 |
| 20 | 29 | 45 | 21 |
| 21 | 58 | 46 | 29 |
| 22 | 51 | 47 | 28 |
| 23 | 34 | 48 | 27 |
| 24 | 46 | 49 | 21 |
| 25 | 59 | | |

THERAPEUTIC EXAMPLE 2

The analgesic activity of the 3-aminoindazole derivative hydrochloric acid salts obtained by Examples 2, 6, 10, 18, 22 and 28 of this invention was measured by the standard method of Randall-Selitto test. In these tests, the amount of the administration of the salts was 100 mg/kg. The results are shown in Table 18.

TABLE 18

| Example No. | Analgesic Coefficient |
|---|---|
| 2 | 0.98 |
| 6 | 1.11 |
| 10 | 1.31 |
| 18 | 1.38 |
| 22 | 1.05 |
| 28 | 0.96 |
| Water (H$_2$O) | 0.8 |

THERAPEUTIC EXAMPLE 3

The acute toxicity of the 3-aminoindazole derivatives and their hydrochloric acid salts obtained by Examples 1–49 of this invention was measured by giving male ddY-strain mice an intravenous injection. The results are shown in Table 19.

TABLE 19

| Example No. | LD$_{50}$ (mg/kg) | Example No. | LD$_{50}$ (mg/kg) |
|---|---|---|---|
| 1 | 146 | 26 | 243 |
| 2 | 101 | 27 | 124 |
| 3 | 143 | 28 | 343 |
| 4 | 97 | 29 | 104 |
| 5 | 175 | 30 | 153 |
| 6 | 91 | 31 | 154 |
| 7 | 143 | 32 | 368 |
| 8 | 358 | 33 | 238 |
| 9 | 347 | 34 | 172 |
| 10 | 233 | 35 | 193 |
| 11 | 115 | 36 | 179 |
| 12 | 334 | 37 | 169 |
| 13 | 359 | 38 | 168 |
| 14 | 95 | 39 | 102 |
| 15 | 144 | 40 | 122 |
| 16 | 184 | 41 | 99 |
| 17 | 143 | 42 | 167 |
| 18 | 102 | 43 | 98 |
| 19 | 144 | 44 | 123 |
| 20 | 98 | 45 | 124 |
| 21 | 184 | 46 | 272 |
| 22 | 102 | 47 | 212 |
| 23 | 152 | 48 | 213 |
| 24 | 367 | 49 | 247 |
| 25 | 356 | | |

What is claimed is:

1. A compound of the formula:

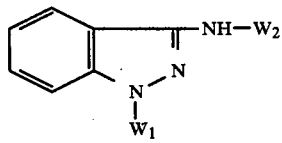

wherein
W$_1$ is a hydrogen atom;
W$_2$ is a

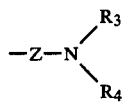

group wherein Z is a C$_{1-6}$ alkylene group or a C$_{1-6}$ alkylene group having a C$_{1-6}$ alkyl group substituent; and R$_3$ and R$_4$ each independently is a hydrogen atom or a C$_{1-6}$ alkyl group and R$_3$ and R$_4$ may form, together with the adjacent nitrogen atom, either a C$_{4-6}$ fully saturated heterocyclic ring or a C$_4$ fully saturated heterocyclic ring containing an additional nitrogen atom, and said fully saturated heterocyclic rings may have at least one C$_{1-6}$ alkyl group, hydroxyl group or halogen atom as a substituent thereon;

or a pharmaceutically acceptable acid addition salt thereof.

2. The compound of claim 1 of the formula (II):

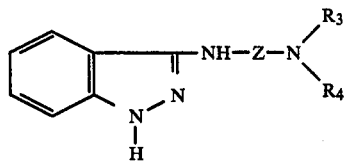

wherein; Z is a C$_{1-6}$ alkylene group or propylene group having a C$_{1-4}$ alkyl group substituent; and R$_3$ and R$_4$ each independently is a C$_{1-6}$ alkyl group and R$_3$ and R$_4$ may form, together with the adjacent nitrogen atom, either a C$_{4-6}$ fully saturated heterocyclic ring or a C$_4$ fully saturated heterocyclic ring containing an additional nitrogen atom and said fully saturated heterocyclic rings may have at least one methyl group, hydroxyl group, chlorine atom, bromine atom or iodine atom as a substituent thereon.

3. The compound of claim 2, wherein Z is ethylene group, n-propylene group, n-hexylene group, 3-methylpropylene group or 3-(2-methylpropyl)propylene group.

4. The compound of claim 3, wherein R$_3$ and R$_4$ are both C$_{1-4}$ alkyl groups.

5. The compound of claim 3, wherein R$_3$ and R$_4$ form, together with the adjacent nitrogen atom, either a C$_{4-6}$ fully saturated heterocyclic ring or a C$_{4-6}$ fully saturated heterocyclic ring containing an additional nitrogen atom and said fully saturated heterocyclic rings may have at least one methyl group, hydroxyl group, chlorine atom, bromine atom or iodine atom as a substituent thereon.

6. The compound of claim 3, wherein

is piperidino group.

7. The compound of claim 2, wherein Z is n-propylene group; and

is pyrrolidino group, homopiperidino group, piperazino group, 2-methylpiperidino group, 2,6-dimethylpiperidino group, 4-hydroxypiperidino group, 4-chloropiperidino group or 4-methylpiperazino group.

* * * * *